(12) United States Patent
Davis et al.

(10) Patent No.: US 9,346,721 B2
(45) Date of Patent: May 24, 2016

(54) HYDROCARBON CONVERSION

(71) Applicant: ExxonMobil Chemical Patents Inc., Baytown, TX (US)

(72) Inventors: Stephen Mark Davis, Dawsonville, GA (US); Mark L. Merrifield, Houston, TX (US); Keith H. Kuechler, Friendswood, TX (US); Loren K. Starcher, Sugarland, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 219 days.

(21) Appl. No.: 14/280,831

(22) Filed: May 19, 2014

(65) Prior Publication Data

US 2014/0378728 A1 Dec. 25, 2014

Related U.S. Application Data

(60) Provisional application No. 61/838,922, filed on Jun. 25, 2013.

(30) Foreign Application Priority Data

Aug. 8, 2013 (EP) ...................... 13179760

(51) Int. Cl.
| | | |
|---|---|---|
| C07C 4/02 | (2006.01) | |
| C07C 4/04 | (2006.01) | |
| C07C 5/35 | (2006.01) | |
| C07C 5/32 | (2006.01) | |
| C01B 3/24 | (2006.01) | |
| C10G 31/06 | (2006.01) | |
| F02C 3/20 | (2006.01) | |
| C10G 35/00 | (2006.01) | |
| C10G 49/00 | (2006.01) | |
| C10G 9/00 | (2006.01) | |

(52) U.S. Cl.
CPC ... *C07C 5/35* (2013.01); *C01B 3/24* (2013.01); *C07C 4/04* (2013.01); *C07C 5/325* (2013.01); *C10G 9/00* (2013.01); *C10G 31/06* (2013.01); *C10G 35/00* (2013.01); *C10G 49/00* (2013.01); *F02C 3/20* (2013.01); *C01B 2203/1241* (2013.01); *C01B 2203/84* (2013.01)

(58) Field of Classification Search
CPC .................................. C07C 4/02; C07C 4/04
USPC .................................................. 585/648, 652
See application file for complete search history.

(56) References Cited

U.S. PATENT DOCUMENTS

| | | | |
|---|---|---|---|
| 3,320,154 A | 5/1967 | Tokuhisa et al. | |
| 3,738,103 A | 6/1973 | Rudolph et al. | |
| 4,287,377 A | 9/1981 | Maslin et al. | |
| 4,912,282 A | 3/1990 | Klaus | |
| 5,585,530 A | 12/1996 | Gough et al. | |
| 5,639,926 A | 6/1997 | Turner et al. | |
| 5,669,216 A | 9/1997 | Ankersmit et al. | |
| 2009/0100820 A1 | 4/2009 | Prabhu | |
| 2011/0219780 A1 | 9/2011 | Prabhu | |

OTHER PUBLICATIONS

Bozena Silverova, et al., Oxidative Dehydrogenation of Ethane and Propane at Short Contact time, Applied Catalysis A: General, v. 276, issues 1-2 (2004), pp. 17-28.
U.S. Appl. No. 14/280,831, filed May 19, 2014, Thuan D. Dang.

*Primary Examiner* — Thuan D Dang

(57) ABSTRACT

The invention relates to hydrocarbon conversion processes, to equipment useful in such processes, to the products of such hydrocarbon conversion processes and the use thereof, and to the use of energy derived from such processes.

5 Claims, 12 Drawing Sheets

HYDROCARBON CONVERSION

PRIORITY CLAIM

This application claims priority to and the benefit of U.S. Provisional Application No. 61/838,992, filed Jun. 25, 2013 and EP 13179760.7, filed Aug. 8, 2013.

FIELD OF THE INVENTION

The invention relates to hydrocarbon conversion processes, to equipment useful in such processes, to the products of such hydrocarbon conversion processes and the use thereof, and to the use of energy derived from such processes.

BACKGROUND OF THE INVENTION

Conventional hydrocarbon conversion processes can be utilized for producing relatively high-value hydrocarbons, e.g., light olefins such as ethylene, propylene, butylene, etc., from relatively low-value hydrocarbon-containing feeds, such as methane, ethane, propane, naphtha, gas oil, crude oil, heavy oil, etc. One such conventional process is steam cracking, a form of thermal pyrolysis where a feed comprising substantially-saturated hydrocarbon is combined with steam, the steam-hydrocarbon mixture then being pyrolysed in one or more radiantly-heated pyrolysis tubes. Steam cracking is an endothermic process, with heat being provided by combusting fuel in one or more furnaces. The pyrolysis tubes are generally located in a furnace box, and a conventional olefins-production facility may include a plurality of furnaces. The radiant heat flux to the pyrolysis tubes can be derived, e.g., from a plurality of burners located in or near the furnace boxes.

There have been significant efforts directed toward increasing the overall efficiency of pyrolysis processes such as steam cracking. One method for increasing efficiency, as disclosed in U.S. Pat. No. 4,287,377, involves burning a mixture of fuel and pre-heated air in the burner, the air being pre-heated in successive compression, heating, and expansion stages of a gas turbine. Fuel and the expanded combustion effluent are combusted in a burner that is located in the cracking furnace, in order to heat pyrolysis tubes. The process exhibits an efficiency gain because heating the air in a gas turbine enables the use of heavier (less expensive) fuels in the burner. An additional efficiency gain is obtained by utilizing work from the gas turbine's expansion zone for compressing the pyrolysis product in the olefin recovery train. Although utilizing a higher air temperature in the burner's air supply is generally beneficial, the ultimate air temperature is limited by the amount of expansion in the gas turbine's expansion zone. Less expansion generally provides burner air of a higher temperature, but also lessens the expansion zone's ability to produce work.

The gas turbine itself can be made more efficient, e.g., by pretreating the gas turbine's fuel, as disclosed in U.S. Pat. No. 5,669,216. The patent discloses decompressing combustion effluent from the gas turbine's combustion chamber in the turbine's expander. Heat is indirectly transferred from the expanded combustion effluent to a hydrocarbon feed in order to upgrade the feed to a higher heat-value fuel for the gas turbine's combustion chamber. As an example, the patent discloses using the indirect heating to upgrade a biogas, LPG, naphtha, or kerosene feed by steam cracking. Further efficiencies can be realized by indirectly transferring heat from the expanded combustion effluent to produce steam for powering a steam turbine. Undesirably, utilizing the steam-cracked product as a gas turbine fuel represents the loss of valuable olefinic products.

It is desired to utilize gas turbine technology to further increase hydrocarbon conversion process efficiency, and in particular to obtain an increase in both efficiency and the amount of recovered olefinic products. It is also desirable to do so without appreciably lessening the amount of power produced by the process, e.g., to obtain an increase in both efficiency and the amount of recovered olefinic products without appreciably decreasing the net work obtained from the gas turbine.

SUMMARY OF THE INVENTION

In an embodiment, the invention relates to a hydrocarbon conversion process, comprising:
  (a) providing a first and second mixtures, the first mixture being in the vapor phase and the second mixture comprising ≥10.0 wt. % of saturated hydrocarbon molecules based on the weight of the second mixture;
  (b) compressing the first mixture;
  (c) transferring heat to the compressed first mixture to produce an effluent;
  (d) optionally expanding the effluent to produce power, wherein at least a portion of the power is utilized for the compressing; and
  (e) producing a third mixture by reacting a second mixture and indirectly transferring of heat between the third mixture and the effluent.

Optionally, the hydrogen transfer of step (e) is catalytic hydrogen transfer, e.g., exothermic catalytic hydrogen transfer. The saturated hydrocarbon can comprise, e.g., ≥90.0 wt. % propane, based on the weight of the saturated hydrocarbon. Optionally, the compressing and expanding are performed in compression and expansion zones of one or more gas turbines, and substantially no heat is added to the expanded effluent before step (e). The process can further comprise producing steam by indirectly transferring heat to water from one or more of (i) the third mixture, (ii) the effluent, or (iii) the expanded effluent; wherein:
  the power produced in step (d) is shaft power;
  at least a portion of steam produced from the indirect transfer of heat is expanded in a steam turbine to produce additional shaft power; and
  ≥10.0% of the shaft power and/or ≥10.0% of the additional shaft power is converted to electricity.

In another embodiment, the invention relates to a hydrocarbon conversion process, comprising:
  (a) providing first and second mixtures, the first mixture being in the vapor phase and the second mixture comprising ≥10.0 wt. % of saturated hydrocarbon molecules based on the weight of the second mixture;
  (b) compressing the first mixture;
  (c) transferring heat to the compressed first mixture to produce an effluent;
  (d) reacting the second mixture, wherein the reacting includes (i) a second transfer of heat, the second transfer of heat being an indirect transfer of heat between the second mixture and the effluent, and (ii) a conversion of ≥5.0 wt. % of the second mixture's saturated hydrocarbon molecules, based on the weight of saturated hydrocarbon molecules in the second mixture, to produce a third mixture comprising products of the conversion; and
  (e) expanding the effluent to produce power, wherein (i) at least a portion of the power being utilized for the compressing and (ii) ≥50.0% of the expanding is performed after the indirect heat transfer.

In yet another embodiment, the invention relates to a hydrocarbon conversion process, comprising:
(a) providing first and second mixtures, the first mixture being in the vapor phase and the second mixture comprising ≥10.0 wt. % of saturated hydrocarbon molecules based on the weight of the second mixture;
(b) compressing the first mixture;
(c) dividing the compressed first mixture into at least first and second portions;
(d) transferring heat to the first portion to produce a first effluent;
(e) expanding the first effluent to produce power, wherein at least a portion of the power being utilized for the compressing;
(f) transferring heat to the second portion to produce a second effluent;
(g) combining ≥10.0 wt. % of the expanded first effluent, based on the weight of the expanded first effluent, with ≥10.0 wt. % of the second effluent, based on the weight of the second combustion effluent, to produce a combined effluent; and
(h) reacting the second mixture, wherein the reaction of the second mixture includes (i) an indirect transfer of heat between the second mixture and the combined effluent and (ii) a conversion of ≥5.0 wt. % of the second mixture's saturated hydrocarbon molecules, based on the weight of saturated hydrocarbon molecules in the second mixture, to produce a third mixture comprising products of the conversion.

In yet another embodiment, the invention relates to a hydrocarbon conversion process, comprising:
(a) providing a first and second mixtures, the first mixture being in the vapor phase and the second mixture comprising ≥10.0 wt. % of saturated hydrocarbon molecules based on the weight of the second mixture;
(b) compressing the first mixture;
(c) transferring heat to the compressed first mixture to produce an effluent;
(d) expanding the effluent to produce power, wherein at least a portion of the power is utilized for the compressing; and
(e) exothermically reacting the second mixture to produce a third mixture, and indirectly transferring at least a portion of the heat from the exothermic reaction to the expanded effluent.

DETAILED DESCRIPTION

In certain embodiments, the invention is based on the development of hydrocarbon conversion processes e.g., processes for producing unsaturated hydrocarbon molecules having two or more carbon atoms ("$C_{2+}$ unsaturated hydrocarbons", also known as $C_{2+}$ unsaturates). These embodiments can utilize compression and expansion equipment, including conventional compression and expansion equipment, such as one or more axial compressors and turbo-expanders, including those joined by a rotating shaft such as one or more gas turbines. Although certain aspects of the invention can involve the use of one or more gas turbines, the invention is not limited thereto, and the following description is not meant to foreclose other embodiments within the broader scope of the invention.

Figure 1A:
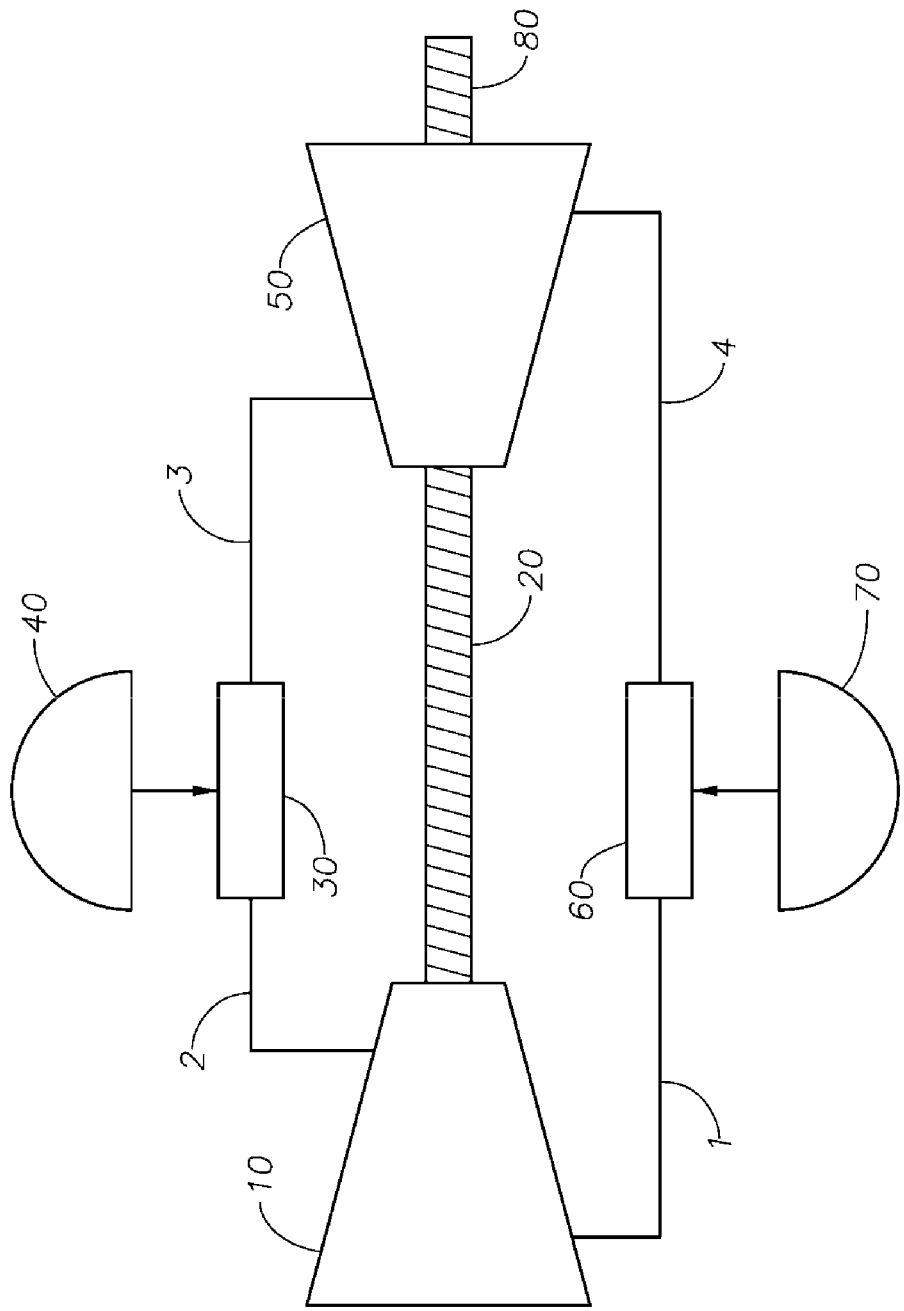
FIG. 1a is a schematic representation of a conventional, closed-cycle gas turbine.

One common form of gas turbine, commonly referred to as a "simple cycle gas turbine", is illustrated schematically in FIG. 1a. The cycle begins with the conduction via conduit 1 of a compressible working fluid, e.g., a vapor such as air, to the inlet of compressing zone 10. Power for the compressing is conveyed to the compressing zone via at least one rotating shaft 20. A compressed working fluid is conducted away from compressor 10 via line 2 to heating zone 30, where heat is transferred from heat source 40 to the compressed working fluid in order to increase the working fluid's temperature. Effluent from the heating zone is conducted via conduit 3 to expansion zone 50, wherein the expansion of the working fluid produces power by rotating shaft 20. Expanded effluent is conducted away from the expansion zone via conduit 4. In a "closed-cycle", simple cycle gas turbine of the type illustrated in FIG. 1a, the expanded effluent is conducted to a cooling zone 60, where heat is conducted from the expanded effluent to a heat sink 70 to produce a cooled effluent. The cooled effluent is then returned to the compressor via line 1 for re-use as the working fluid to complete the cycle.

Approximate values for thermodynamic parameters such as working fluid temperature, working fluid pressure, working fluid flow rate, heat flow, power generated by the expander, power consumed by the compressor, the amount of heat added to the process from the heat source, and the amount of heat withdrawn from the process by the heat sink can be determined for an idealized gas turbine in accordance with the Brayton Cycle. The thermodynamic parameters can be evaluated, e.g., using the methods disclosed in *Energy Conversion*, Kenneth W. Weston, Brooks/Cole, 1992. The Brayton Cycle includes an isentropic compression of the working fluid (where work $W_c$ is done on the working fluid), an isobaric transfer of heat to the working fluid, an isentropic expansion of the heated working fluid (where work $W_t$ is done by the working fluid), and then an isobaric transfer of heat from the working fluid. The difference between the absolute values of the work done by the working fluid during the expansion and the work done on the working fluid during the compression $[|W_t|-|W_c|]$ is the cycle's net work. The net work can be delivered via an output shaft 80 as shaft work, e.g., for powering an electric generator to produce electricity.

Figure 1B:
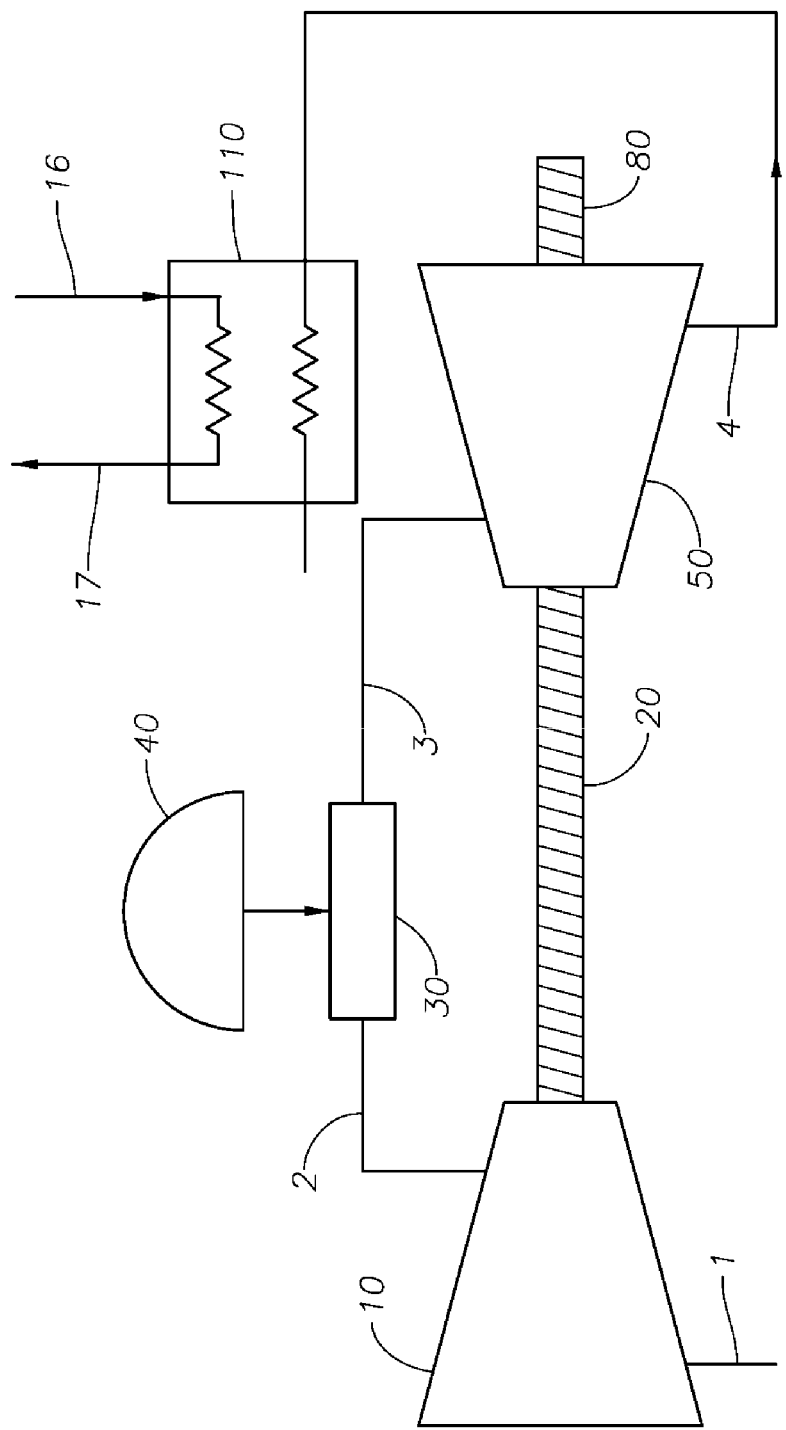
FIG. 1b is a schematic representation of an open-cycle gas turbine having a heat exchanger stage for recovering heat from the turbine's expanded effluent.

It can be convenient to configure a gas turbine to operate in an "open-cycle" configuration, as shown in FIG. 1b. When operating in an open-cycle configuration using air as the working fluid, the air is conducted to the compression zone 10, e.g., using conduit 1, with the compressed air being conducted to heating zone 30 via conduit 2. Effluent from the heating zone is conducted via conduit 3 to expansion zone 50, where the effluent is expanded. The expanded effluent is conducted away via conduit 4. A portion of the work done by the effluent during the expansion is transmitted as shaft work on shaft 20 for powering the compression. Additional shaft work is provided by shaft 80, e.g., for powering equipment such as one or more electric generators for producing electricity. One or more heat exchangers 110 can be used, e.g., to transfer heat from the expanded effluent (conduit 4) to water (or steam, such as low pressure steam, or high pressure steam) provided via conduit 16 with heated water (or heated steam) being conducted away from the heat exchanger via conduit 17.

Figure 2A:
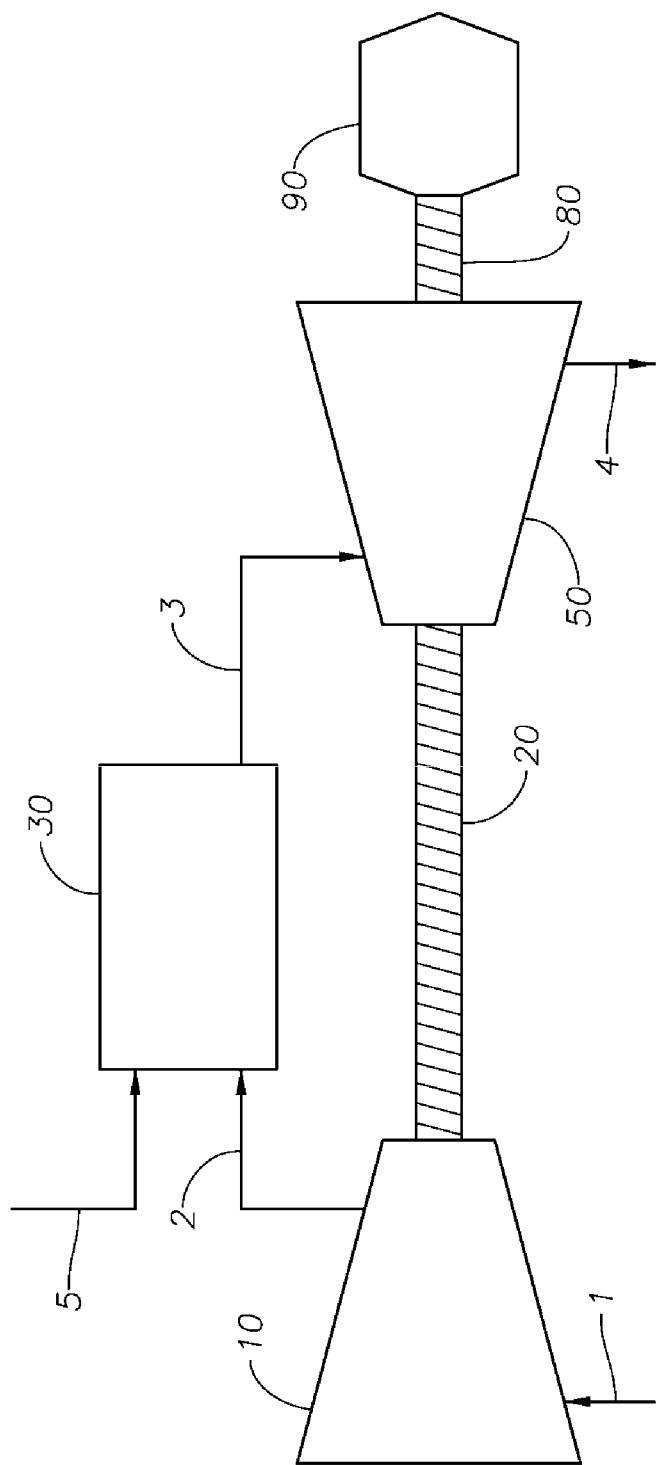
FIG. 2a is a schematic representation of an open-cycle gas turbine, where the heating zone includes at least one combustion zone.

In certain embodiments, e.g., those where the working fluid is an oxygen-containing gas such as air, heating zone 30 includes a combustion zone. Fuel can be conducted to the combustion zone via conduit 5, as shown in FIG. 2a. At least a portion of the working fluid conveyed to the heating zone via conduit 2 is utilized for reacting (e.g., combusting) at least a portion of the fuel, and at least a portion of the heat produced by the combustion is utilized for heating the heating zone's effluent. The effluent, which generally comprises products of the combustion, un-reacted fuel, and un-reacted working fluid, is conducted to expansion zone 50 via conduit 3. Such a gas turbine can operate in a closed cycle configuration, but it is generally more advantageous to operate in an open-cycle configuration, as shown in FIG. 2a.

Figure 2B:
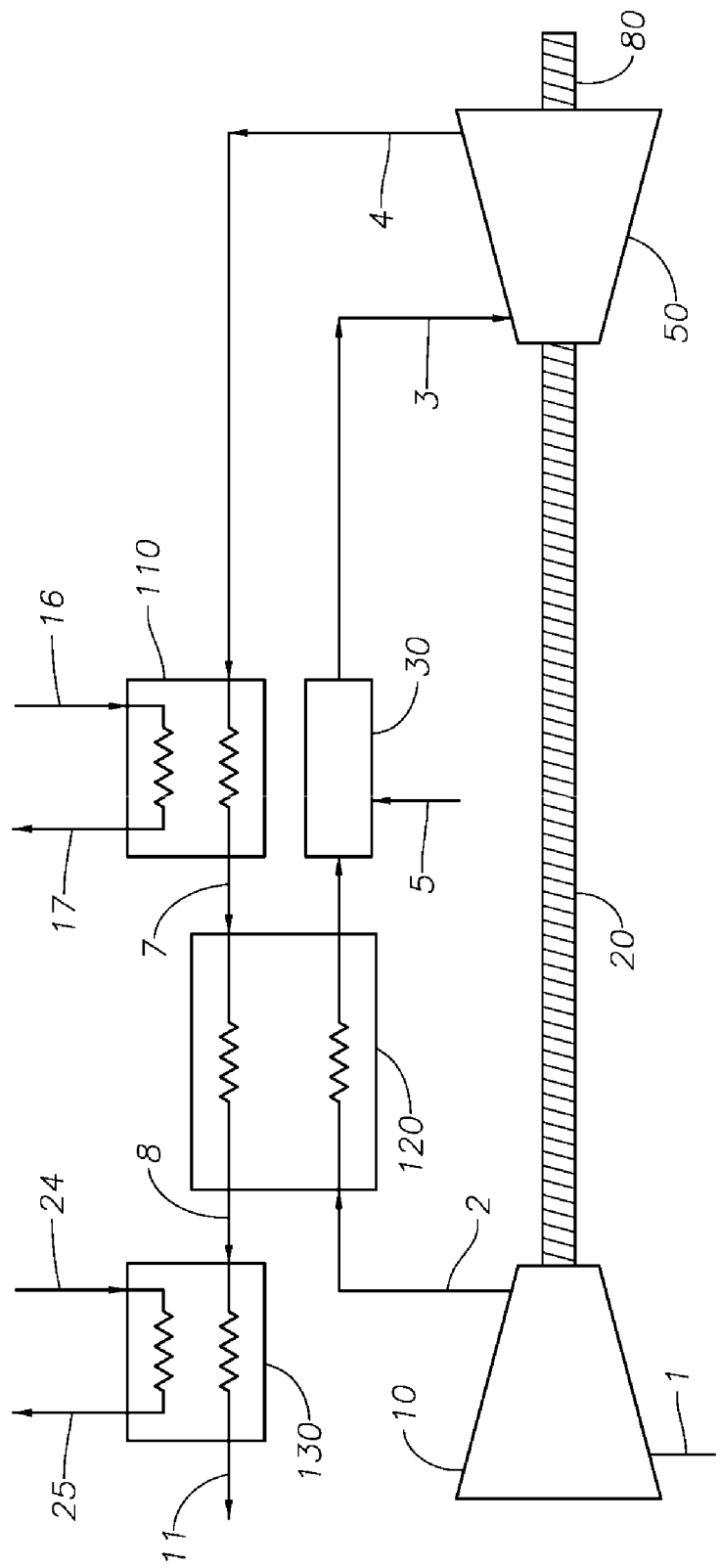
FIG. 2b is a schematic representation of an open-cycle gas turbine having two heat exchanger stages and a regenerator stage downstream of the turbine's expansion zone.

The invention is not limited to any particular gas turbine technology, and can be practiced in combination with other improvements to gas turbine technology, e.g., improvements to gas turbine mechanical, thermal, and chemical efficiencies. For example, the invention is compatible with thermal improvements such as the recovery of heat from the expanded effluent downstream of expansion zone 50, e.g., recovery of heat from the expanded effluent of conduit 4. Gas turbine efficiency can be improved by utilizing one or more regenerator stages 120 downstream of expansion zone 50, as shown in FIG. 2b. When utilizing regenerator 120, heat is transferred from at least a portion of the expanded effluent to at least a portion of the compressed working fluid, in order to lessen the amount of heating needed in heating zone 30, e.g., lessening the amount of fuel needed in a combustion zone associated with heating zone 30. Further efficiencies can be obtained using one or more heat exchangers. For example, one or more heat exchangers (110 and 120 of FIG. 2b) can (i) substitute for regenerator 120 or (ii) can be located upstream and/or downstream of regenerator 120. As in the configurations schematically illustrated in FIG. 1b, one or more heat exchangers 110 can be used, e.g., to transfer heat from the expanded effluent to water (or steam, such as low pressure steam, or high pressure steam) provided via conduit 16 with heated water (or heated steam) being conducted away from the heat exchanger via conduit 17. Expanded effluent having a lower temperature than that of conduit 4, is conducted away (e.g., to regenerator 120) via conduit 7. Similarly, a heat exchanger 130 can be utilized e.g., to transfer heat from the expanded effluent of conduit 8 to water (or steam, such as low pressure steam, or high pressure steam) provided via conduit 24, with heated water (or heated steam) being conducted away from the heat exchanger via conduit 25. A cooled, expanded effluent can be conducted away via conduit 11. Stages 110 and/or 130 can optionally include one or more heat recovery steam generators, the steam can be utilized, e.g., for powering a steam turbine. At least a portion of the power generated by the steam turbine, such as shaft power, can be utilized, e.g., for generating electricity. Optionally, one or more heat exchangers (not shown) can be utilized downstream of heating zone 30 and upstream of turbine 50, e.g., for controlling the inlet temperature of expansion zone 50 to protect the expansion means (e.g., one or more turbines) from thermal damage.

Figure 2C:
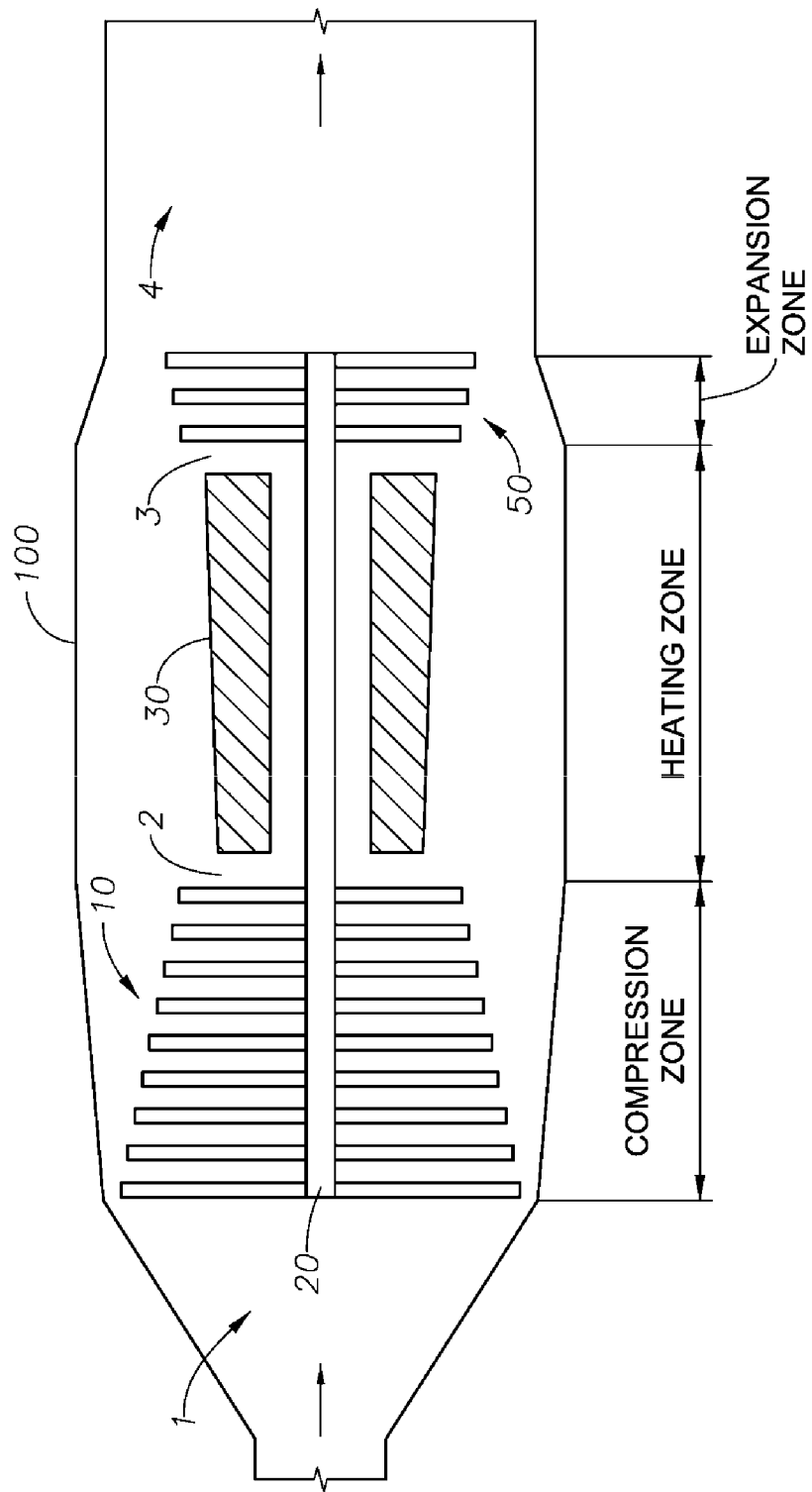
FIG. 2c is a schematic representation of a gas turbine unit having an internal compression zone, heating zone, and expansion zone.

The invention is also compatible with mechanical improvements to gas turbine technology, such as those illustrated in FIG. 2c, where the conduits and components of FIG. 2a are located in a single gas turbine unit 100. The gas turbine unit 100 contains, e.g., a first end for conveying working fluid to the unit, and an internal conduit 1 for diffusing the working fluid and for conveying the working fluid to a compression zone 10 located within the gas turbine unit. The compression zone can contain, e.g., one or more zones of axial compression. Conventional compression means can be utilized, e.g., a plurality of turbofan blades fixed to shaft 20. At least a portion of conduit 2 is also located within gas turbine unit 100, for conveying the compressed working fluid to heating zone 30. Conventional conveying means can be utilized to do this, e.g., one or more conduits, plenums, ducts, baffles, flow directors, etc., (not shown). Generally, fuel is provided to heating zone 30 by one or more conduits (not shown), the fuel being introduced into at least one combustion zone (shaded region within heating zone 30) by one or more nozzles (not shown). When it is advantageous to do so, such as for braking shaft 20 and/or for providing thrust, a portion of the compressed working fluid can be diverted around all or a portion of heating zone 30 (and optionally around expansion zone 50), and, e.g., conducted away from the process. Conventional means can be utilized to do this, such as one or more conduits, plenums, ducts, baffles, flow directors, etc., (not shown). Conduits 3 and 4, and expansion zone 50, can also be located within gas turbine unit 100. More than one expansion zone can be utilized, with one or more expansion means (such as one or more turbo-expanders operated in parallel, series, and/or series-parallel) being located in each of the expansion zones. At least a segment of conduit 4, e.g., a segment proximate to expansion zone 50, can be in the form of a plenum or duct, as shown in FIG. 2c.

The invention is also compatible with the practice of improvements in the chemical efficiency of gas turbine processes, e.g., (i) by upgrading fuel to the combustion zone in order to increase heat output during combustion (as disclosed in U.S. Pat. No. 5,669,216, which is incorporated by reference herein in its entirety) and/or (ii) by combusting fuel and the expanded combustion effluent of a gas turbine in a burner located in a furnace for endothermically cracking a hydrocarbon feed to produce ethylene (as disclosed in U.S. Pat. No. 4,287,377, which is incorporated by reference herein in its entirety).

Certain embodiments of the invention will now be described in more detail, these embodiments utilizing at least one gas turbine having at least one rotating shaft, e.g., an open-cycle gas turbine. The gas turbine is optionally utilized in combination with at least one steam turbine, the steam turbine having a rotating shaft that can be the same as that of the gas turbine and/or a different rotating shaft. The invention is not limited to these embodiments, and this description is not meant to foreclose other embodiments within the broader scope of the invention.

Conversion Processes Utilizing at Least One Gas Turbine

It is observed that when operating a gas turbine under conventional operating conditions that it is desirable to increase the temperature of the expanded air in order to make the expanded air more useful as a heat source for chemical conversion reactions. In the following example, a conventional gas turbine is operated using conventional operating conditions. The example shows that the expanded working fluid conducted away from the gas turbine's expansion stage does not have a sufficient temperature to support reactions such as the pyrolysis of methane or ethane to produce $C_{2+}$ unsaturates.

In this example of conventional gas turbine technology, an open cycle gas turbine utilizes a working fluid comprising ≥90.0 wt. % of atmospheric air based on the weight of the working fluid. The atmospheric air is of ambient temperature and pressure, i.e., a temperature ($T_1$) of 300° K and a pressure ($P_1$) 1 bar absolute. The air is provided to the gas turbine's compression zone at a flow rate (dm/dt) of 500 kilograms per second ("kg/s"). The conventional gas turbine compresses the working fluid to a pressure of 5 bar absolute ($P_2$) and temperature $T_2$, with the compressed working fluid then being heated at a constant pressure in the gas turbine's combustion zone. The heating is carried out by combusting a fuel having a higher heating value of approximately $52 \times 10^6$ joules/kilogram ("J/kg"), e.g., natural gas. In order to prevent thermal damage to the turbo-expander, the amount of heating is regulated to provide a temperature of the heated working fluid at the expansion zone's inlet ("$T_3$") of ≥1200° K. The expansion zone's turbo-expander decreases the pressure of the heated working fluid from 5 bar absolute ($P_3$) to produce expanded air having a pressure ($P_4$) of 1 bar absolute and a temperature $T_4$. The expanded working fluid is then conducted away from the gas turbine.

Approximate values for the temperature of the compressed air before heating, the temperature of the expanded air, the power required by the compressor, and the power produced by the expander, and the required mass flow rate of the fuel can be obtained by modeling the gas turbine as undergoing a Brayton Cycle. Accordingly, using the relationship $T_2=T_1*(P_2/P_1)^{(\gamma-1)/\gamma}$, with $\gamma=1.4$ (approximate value for air), then $T_2=475°$ K. Using the approximate value for the heat capacity of air at constant pressure, $C_p=1.005$ kJ/(kg$_*$° K), the shaft power needed to compress the air can be determined from the relationship $(dW_c/dt)=C_p*(dm/dt)(T_2-T_1)=88 \times 10^6$ watts.

An approximate value for amount of heat per unit time (dQ/dt) needed to increase the temperature of the air in the heating zone from $T_2$ to $T_3$ can be approximated from the relationship $dQ/dt=C_p*(dm/dt)(T_3-T_2)=364 \times 10^6$ watts. This heat is provided by burning the natural gas fuel in the combustion zone, the natural gas having a high heating value of approximately $52 \times 10^6$ J/kg. An approximate value for the mass flow rate of fuel needed to produce $364 \times 10^6$ watts of heating by combustion can be determined by dividing $364 \times 10^6$ watts by the high heating value of the fuel, i.e., the fuel mass flow rate is approximately 8.8 kg/s. Since the amount of fuel provided to the heating zone is only about 2% (mass basis) of the amount of air, it is conventional to ignore the masses of fuel and the products of fuel combustion when calculating the thermal and thermo-mechanical characteristics of the gas turbine. $T_4$ can then be approximated by the relationship $T_4=T_3*(P_4/P_3)^{(\gamma-1)/\gamma}$, where $\gamma$ has the value for air (1.4). $T_4$ is therefore approximately 758° K. The shaft power provided to the turbo-expander by the expanding air can be approximated by the relationship $(dW_t/dt)=C_p*(dm/dt)(T_3-T_4)=222 \times 10^6$ watts, where $C_p$ has the value for air (the masses of combustion products and un-combusted fuel are sufficiently small that it is conventional to ignore them).

The amount of shaft power available for electric power generation is approximately equal to the difference between the power generated by the turbo-expander ($222 \times 10^6$ watts) and the power consumed by the compressor ($88 \times 10^6$ watts) $=134 \times 10^6$ watts. Approximately 40% (88/222) of the shaft power produced by the turbo-expander is utilized for powering the compressor. The cycle's thermal efficiency can be approximated by dividing the available shaft power ($134 \times 10^6$ watts) by the amount of power consumed in heating the air in the heating zone ($364 \times 10^6$ watts), or about 37%.

The approximate value of $T_4$, about 758° K, or 485° C., is generally not sufficient for reactions such as the pyrolysis of methane to produce acetylene, or even the steam cracking of hydrocarbons to produce ethylene. U.S. Pat. No. 4,287,377 discloses a method for overcoming this deficiency by heating the expanded air from the turbo-expander to a temperature sufficient for the pyrolysis of methane to acetylene. The method disclosed in the patent includes conducting the expanded air to a burner, the burner being located within a pyrolysis furnace. The methane is conducted into tubes within the pyrolysis furnace, the tubes being indirectly heated to pyrolysis temperatures by combusting at least a portion of the expanded air with fuel in a firebox, the firebox being located adjacent to the tubes. The process is inefficient for at least the reasons (i) that cooling will occur as the expanded air is conveyed from the turbo-expander to the firebox, further increasing the process's demand for fuel and (ii) at least a second burner (located in the furnace's firebox) is needed in addition to the burner of the gas turbine.

In certain aspects of the invention, these difficulties are overcome by locating tubes in which one or more reactions can occur (e.g., the pyrolysis of methane) downstream of at least a portion of the gas turbine's heating zone and upstream of at least a portion of the gas turbine's expansion zone. Certain embodiments employing this aspect of the invention are illustrated schematically in FIG. 3a.

I. Embodiments Having a Reaction Zone Upstream of the Expansion Zone

In certain embodiments of the invention, first and second mixtures are provided to the process, the first mixture being in the vapor phase and the second mixture comprising ≥10.0 wt. % of saturated hydrocarbon molecules based on the weight of the second mixture. Optionally, the first mixture comprises ≥10.0 wt. % oxidant based on the weight of the first mixture.

Figure 3A:
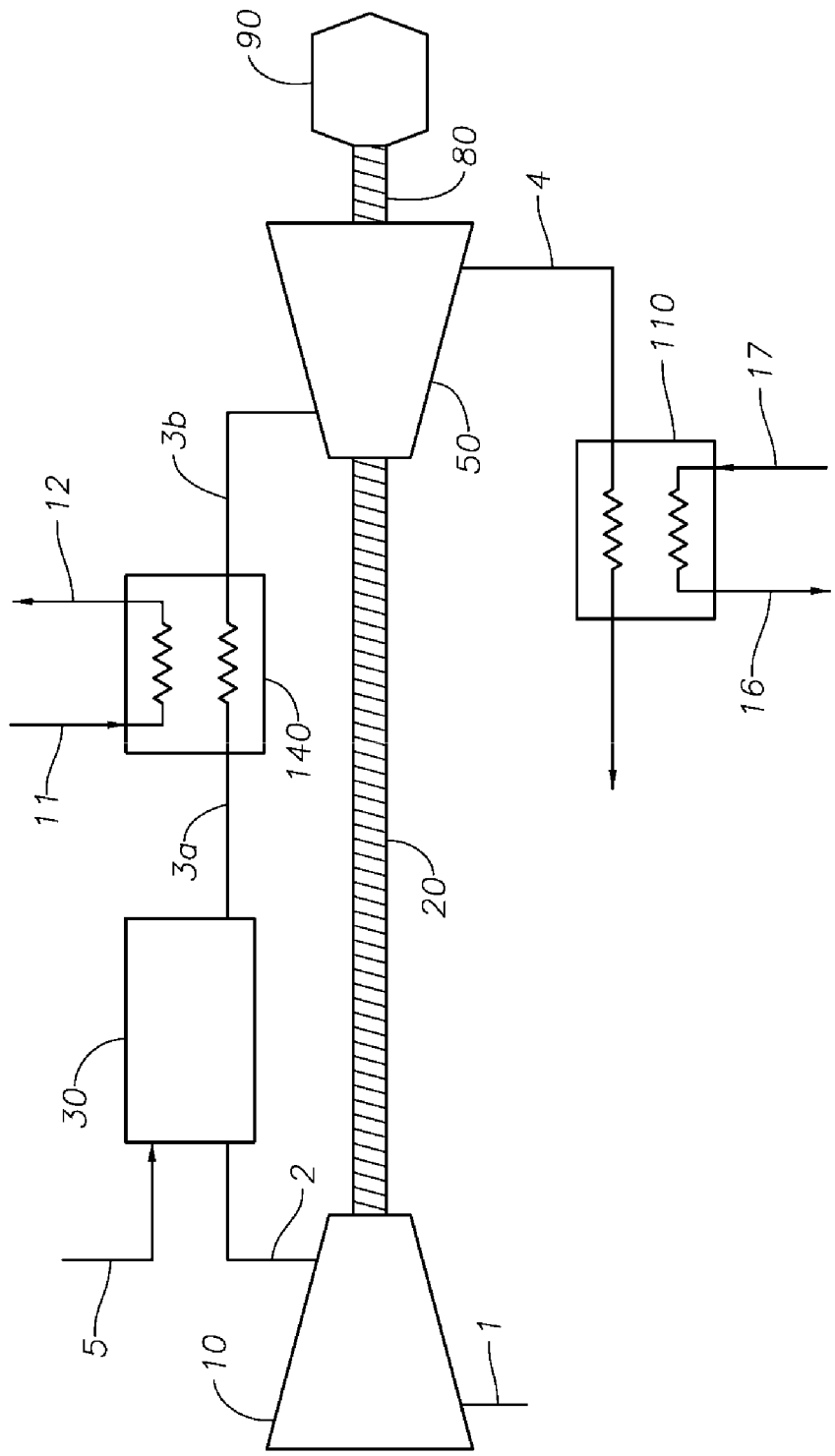
FIG. 3a is a schematic representation of an open-cycle gas turbine having a reaction zone downstream of the heating zone and upstream of the expansion zone.

Referring to FIG. 3a, the first mixture (the working fluid) is conducted via conduit 1 to compression zone 10, where the first mixture is compressed. Conventional gas turbine compression can be used, but the invention is not limited thereto. For example, certain embodiments of the invention utilize compressors driven by shaft power, such as those typically utilized in gas turbines. The compressors can be operated, e.g., in series, parallel, or series-parallel. The compressed first mixture is conducted via conduit 2 to heating zone 30, where heat is transferred to the compressed first mixture (a first transfer of heat). Conventional gas-turbine heating means can be utilized in the heating zone, but the invention is not limited thereto. For example, when the first mixture includes atmospheric air, e.g., ≥90.0 wt. % of atmospheric air based on the weight of the first mixture, the heating zone can comprise one or more combustion zones for at least partially combusting a fuel with at least a portion of the compressed first mixture's air. A fourth mixture comprising fuel can be conducted to the combustion zone via conduit 5, for example. Effluent from the heating zone, e.g., a compressed, heated first mixture, is conducted away via conduit 3a to reaction zone 140. The second mixture is conducted to zone 140 via conduit 11, and is reacted in zone 140, the reaction includes (i) a second transfer of heat, the second transfer of heat being an indirect transfer of heat between the second mixture and the compressed, heated first mixture, and (ii) a conversion of ≥5.0 wt. % of the second mixture's saturated hydrocarbon molecules, based on the weight of saturated hydrocarbon molecules in the second mixture, to produce a third mixture comprising products of the conversion. Although the indirect heat transfer of zone 140 can occur proximate to expansion zone 50, generally ≥50.0% of the expanding is performed after the indirect heat transfer. A third mixture, which includes (i) at least a portion of the conversion products and (ii) any unreacted second mixture, is conducted away via conduit 12.

Conventional reactors are suitable for use in zone 140, e.g., conventional tube reactors, but the invention is not limited thereto. When the conversion of zone 140 is exothermic, the compressed effluent conducted away from zone 140 via conduit 3b is generally at a higher temperature than that of conduit 3a. When the conversion of zone 140 is endothermic, the compressed effluent conducted away from zone 140 via conduit 3b is generally at a lower temperature than that of conduit 3a. When the conversion of zone 140 is neither endothermic nor exothermic, the compressed effluent conducted away from zone 140 via conduit 3b is generally can be, e.g., at substantially the same temperature as that of conduit 3a. Reactions of the second mixture occurring within conversion zone 140 can include, e.g., one or more of cracking, hydroprocessing, reforming, pyrolysis, thermal pyrolysis, thermal hydrogen transfer, or catalytic hydrogen transfer (including catalytic oxidative hydrogen transfer). In embodiments where the second mixture conversion is endothermic, heat can be added downstream of zone 140 but upstream of zone 50, in order to maintain efficiency in the expansion zone. This can be done by exposing the compressed effluent to a temperature ≥700.0° C. Conventional supplemental firing upstream of zone 50 can be utilized to do this, but the invention is not limited thereto. In embodiments where the conversion of the second mixture is exothermic, the flow of the second mixture to zone 140 can be lessened and/or interrupted from time to time in order to lessen the risk of exceeding temperature limitations (e.g., loss of elastic modulus) of the internals of the expansion zone. In other embodiments, the amount of heat produced in zone 30 is lessened, e.g., by lessening the amount of fuel provided via line 5.

Continuing with reference to FIG. 3a, the compressed effluent is conducted away from zone 140 to expansion zone 50 for expanding the compressed effluent to produce power. Conventional expanding equipment can be utilized in zone 50, such as one or more turbo-expanders (operating, e.g., in series, parallel, or series-parallel). The compressed effluent is expanded in zone 50 to produce power, with at least a portion of the power being utilized for the compressing. When the compression and expansion zones are connected by a common shaft 20 as shown in FIG. 3a, the power can include shaft power. A portion of the shaft power produced by the expansion can be utilized, e.g., for generating electricity using one or more generators 90, the generators being powered by shaft 80. Expanded effluent is conducted away via conduit 4, e.g., for storage, further processing, or other suitable disposition. Certain embodiments utilize optional stage 110, containing, e.g., one or more heat recovery steam generators. Heat can be indirectly exchanged between the effluent in conduit 4 and steam conducted to stage 110 via conduit 17, with superheated steam being conducted away via conduit 16. The superheated steam can be utilized for operating a steam turbine, e.g., to produce additional power, such as additional shaft power. One or more conduits, e.g., one or more of conduits 1, 2, 3a, 3b, 4, and 5 can be, e.g., piping, tubing, and the like. Alternatively, one or more of these can comprise one or more channels, ducts, etc., located within or partly within the gas turbine unit, of the kind shown in FIG. 2c. Likewise, one or more of zones 10, 30, 140, 50, and 110 can be located in regions within or partly within a gas turbine unit of the kind shown in FIG. 2c.

In certain embodiments, a portion of the shaft power obtained from expansion zone 50 is utilized for additional compression, e.g., for compressing at least a portion of the third mixture. For example, when the third mixture comprises olefin, compression of the third mixture can be utilized during olefin upgrading and/or recovery.

In certain embodiments of the invention where the process is operated in one or more gas turbines, the fourth mixture can comprise ≥10.0 wt. % fuel based on the weight of the fourth mixture. Optionally, the compressing of zone 10, the heat transfer of zone 30, and the expanding of zone 50 are conducted in a gas turbine to produce shaft power. Optionally, the first heat transfer includes exposing the first mixture to a temperature ≥1.0×10$^3$° C. by reacting ≥50.0 wt. % of the fourth mixture's fuel, based on the weight of the fourth mixture's fuel, with at least a portion of the compressed first mixture's oxidant.

In certain embodiments, the first mixture comprises ≥90.0 wt. % air, based on the weight of the first mixture, e.g., atmospheric air of ambient temperature and pressure (300° K and 1 bar). The fourth mixture can comprise, e.g., ≥90.0 wt. % hydrocarbon based on the weight of the fourth mixture. The second mixture can comprise, e.g., ≥90.0 wt. % alkane based on the weight of the second mixture. When the second mixture is subjected, e.g., to alkane thermal pyrolysis in zone 140, such as methane or ethane cracking (including steam cracking), the third mixture can comprise, e.g., ≥1.0 wt. % $C_{2+}$ unsaturates that are produced by the thermal pyrolysis, based on the weight of the third mixture. For example, thermal pyrolysis conditions in reaction zone 140 can include thermal pyrolysis conditions, such as those where the second mixture is exposed to a temperature ≥800° C., e.g., ≥1000° C., such as ≥1200° C., or ≥1400° C., such as in the range of 1200° C. to 1500° C.

In certain embodiments the process further comprises producing steam by indirectly transferring heat to water from one or more of (i) the third mixture, (ii) the effluent, or (iii) the expanded effluent (as illustrated in stage 110 of FIG. 3a). Optionally, at least a portion of the steam is produced by an indirect transfer of heat from the effluent or expanded effluent during at least one of (i) before the heating in zone 30 and the expanding in zone 50, (ii) before the expanding in zone 50 but after the heating in zone 30, (iii) during the expanding of zone 50, or (iv) after the expanding of zone 50. At least a portion of the steam produced from this indirect transfer of heat can be expanded to provide additional power, e.g., in a steam turbine for producing additional shaft power. If desired, at least a portion of the additional shaft power can be used for powering one or more electric generators for producing electricity.

Figure 3B:
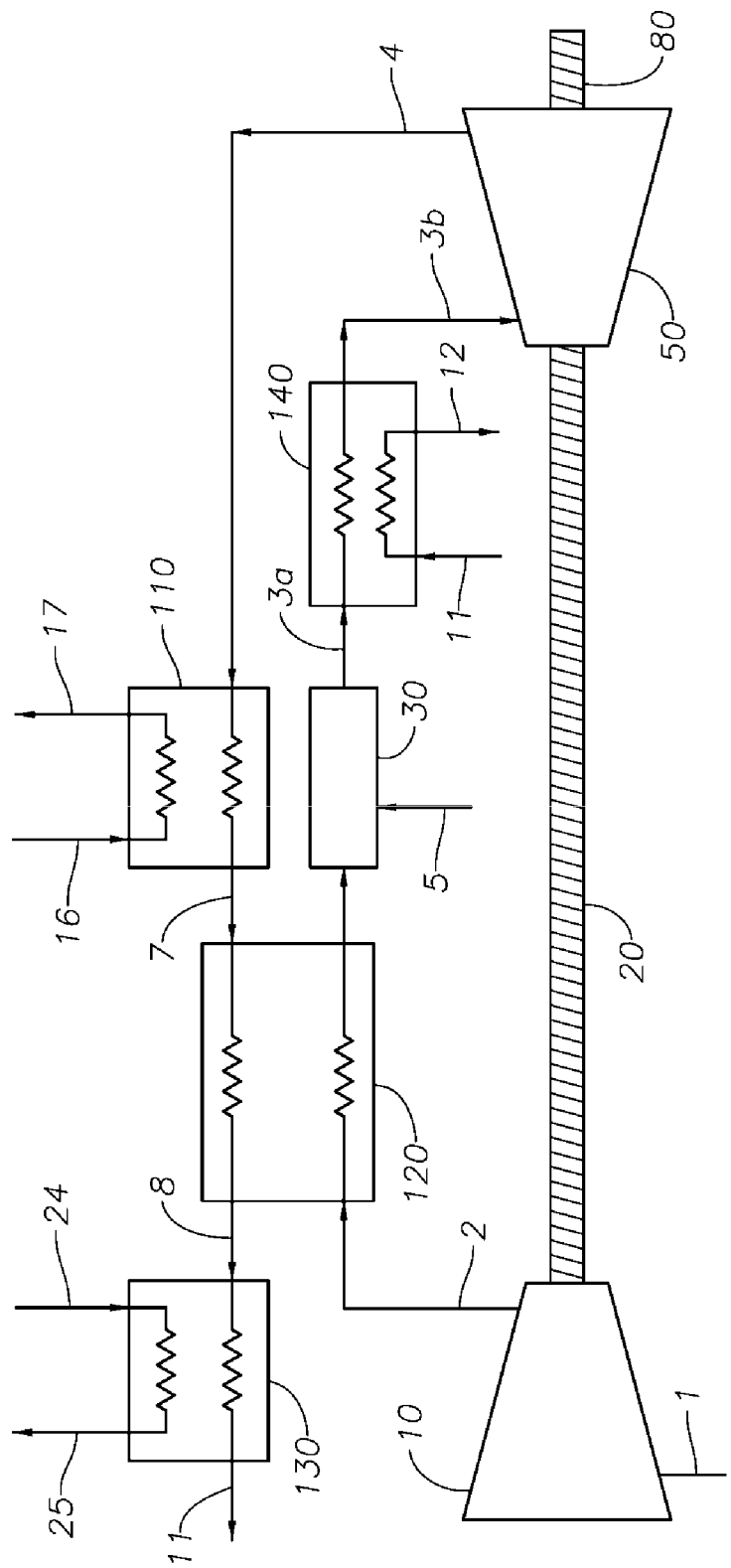
FIG. 3b is a schematic representation of an open-cycle gas turbine having (i) a reaction zone downstream of the heating zone and upstream of the expansion zone and (ii) two heat exchanger stages and a regenerator stage downstream of the turbine's expansion zone.
Figure 3C:
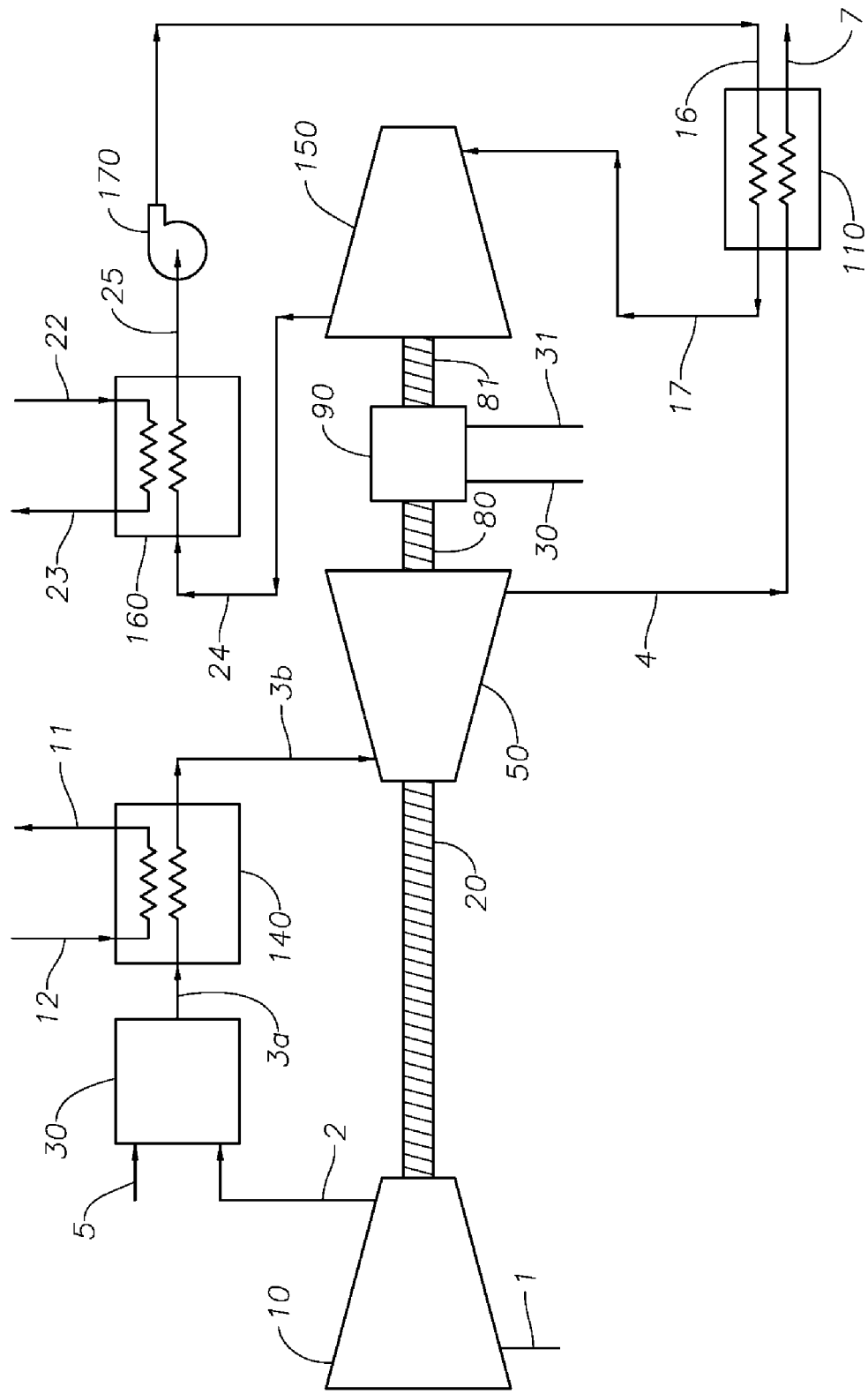
FIG. 3c is a schematic representation of an embodiment utilizing an open-cycle gas turbine and a steam turbine, the steam turbine being powered by steam produced by and indirect transfer of heat from the gas turbine's expanded effluent.
Figure 3D:
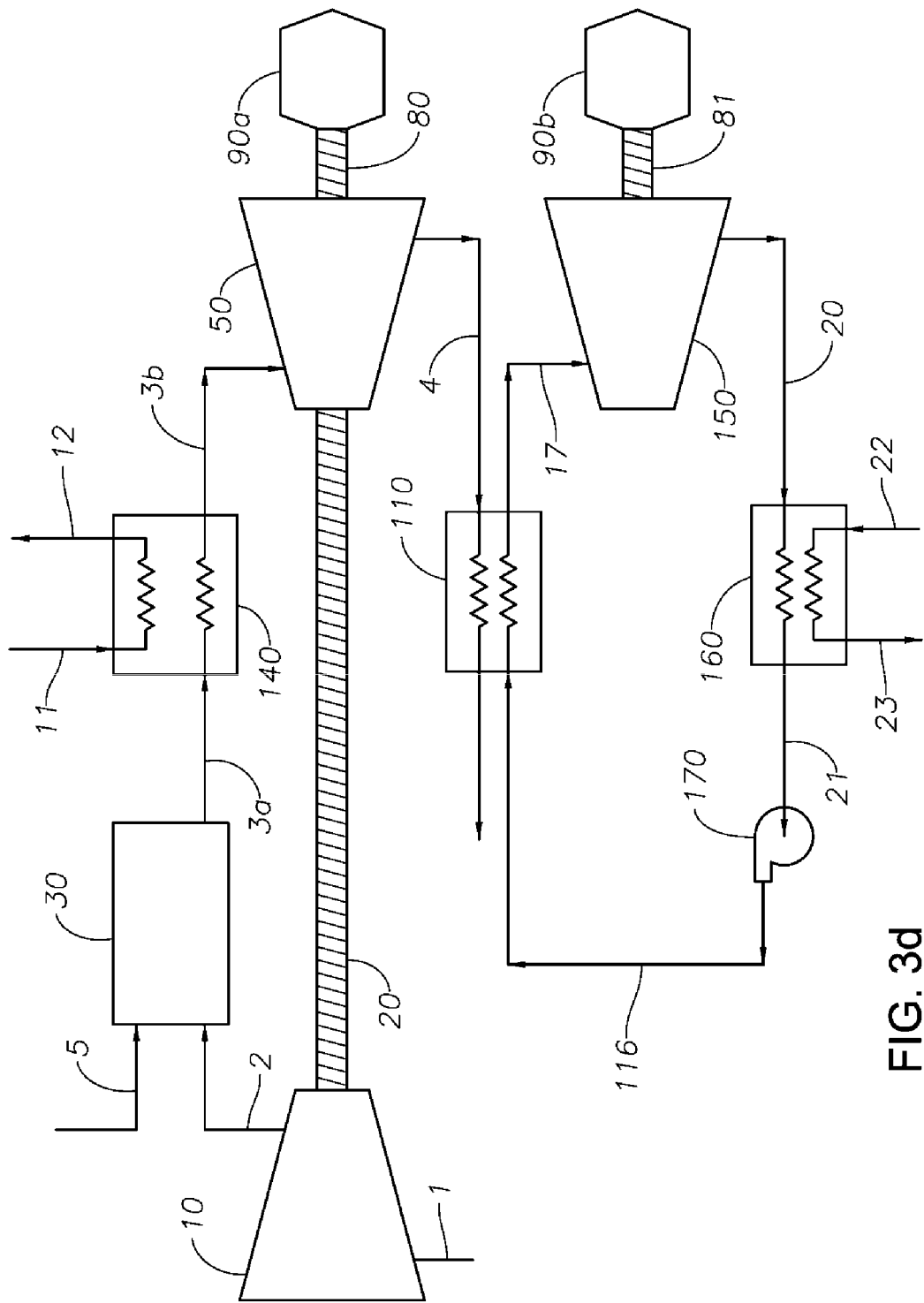
FIG. 3d is a schematic representation of an open-cycle gas turbine of another embodiment utilizing an open-cycle gas turbine and a steam turbine, the steam turbine being powered by steam produced by and indirect transfer of heat from the gas turbine's expanded effluent.

Aspects of these embodiments of the invention are further illustrated schematically in FIGS. 3b, 3c, and 3d. In FIG. 3b, which is analogous to the conventional process illustrated in FIG. 2b, an optional heat recovery steam generator 110, an optional regenerator 120, and an optional heat exchanger 130 (which can be a second heat recovery steam generator) are located in series downstream of expansion zone 50. Process features having the same index numbers in FIG. 3b as those of FIG. 2b perform similar (or the same) functions.

Certain embodiments of the invention utilizing a steam turbine for increased efficiency are schematically illustrated in FIG. 3c. As shown in the figure, expanded effluent from expansion zone 50 is conducted via conduit 4 to heat recovery steam generator 110, where heat is transferred from the expanded effluent to water (e.g., boiler water, wet steam, steam, etc.), the water being provided via conduit 16. Heated steam (e.g., superheated steam) is conducted via conduit 17 to steam turbine 150 where the steam is expanded to produce additional power, e.g., additional shaft power. As shown in the figure, shaft power from gas turbine obtained via shaft 80 can be combined with the additional shaft power from steam turbine 150 obtained via shaft 81, with the combined shaft power being utilized for powering a load 90, e.g., one or more electric generators for producing electricity. The electricity can be conducted away from the process via one or more electric conductors, e.g., conductors 30 and 31. In certain embodiments, the expanded steam can be condensed for re-use. For example, expanded steam is conducted via conduit 24 from steam turbine 150 to condenser 160. A cooling fluid, e.g., cooling water, is conducted to the condenser via line 22, and heat is transferred from the expanded steam to the cooling fluid. Cooling fluid is conducted away via conduit 23 from condenser 160. At least a portion of the water that is condensed from the expanded steam can be conducted via line 25 to pump 170, the pump being utilized for transferring the condensed water to line 16 for re-use in the heat recovery steam generator. Except for the production of additional shaft power, the process can be operated in substantially the same way as the embodiments illustrated in FIGS. 3a and 3b. Process features having the same index numbers in FIG. 3c as those of FIGS. 3a and 3b perform similar (or the same) functions. Although it can be beneficial to provide the additional shaft power to the same shaft or a side shaft as that utilized for transferring the shaft power, as shown in FIG. 3c, this is not required, and in other embodiments the additional power is transferred from the steam turbine on a second shaft that is independent of the shaft utilized for transferring shaft power from the gas turbine. For example, the embodiments illustrated schematically in FIG. 3d utilize (i) shaft 80 for transferring shaft power from gas turbine 50 to load 90a and (ii) shaft 81 for transferring additional shaft power from steam turbine 150 to load 90b. Except for the differences in the transfer of additional shaft power, the process can be operated in substantially the same way as the embodiments illustrated in FIG. 3c. Process features having the same index numbers in FIGS. 3a-d as those of FIGS. 1a, 1b, and 2a-c perform similar (or the same) functions.

II. Embodiments Utilizing Supplemental Heating

In certain embodiments, the invention relates to a hydrocarbon conversion process utilizing supplemental heating of at least a portion of the compressed working fluid. As in Embodiments I, the process utilizes a first mixture (the working fluid) and a second mixture (a hydrocarbon-containing mixture), the first mixture being in the vapor phase and the second mixture comprising ≥10.0 wt. % of saturated hydrocarbon molecules based on the weight of the second mixture. The process features compressing the first mixture, dividing the compressed first mixture into at least first and second portions, and transferring heat to the first portion to produce a first effluent. At least a portion of the first effluent is expanded to produce power, wherein at least a portion of the power being utilized for the compressing. The process further comprises transferring heat to the second portion (the supplemental heating) to produce a second effluent, and combining the expanded first effluent with the second effluent. For example, ≥10.0 wt. % of the expanded first effluent, based on the weight of the expanded first effluent, can be combined with ≥10.0 wt. % of the second effluent, based on the weight of the second combustion effluent, to produce a combined effluent. The process further comprises reacting the second mixture, wherein the reacting of the second mixture includes (i) an indirect transfer of heat between the second mixture and the combined effluent and (ii) a conversion of ≥5.0 wt. % of the second mixture's saturated hydrocarbon molecules, based on the weight of saturated hydrocarbon molecules in the second mixture, to produce a third mixture comprising products of the conversion. The reacting can include, e.g., one or more of the reactions specified for the second mixture in Embodiments I.

Figure 4:
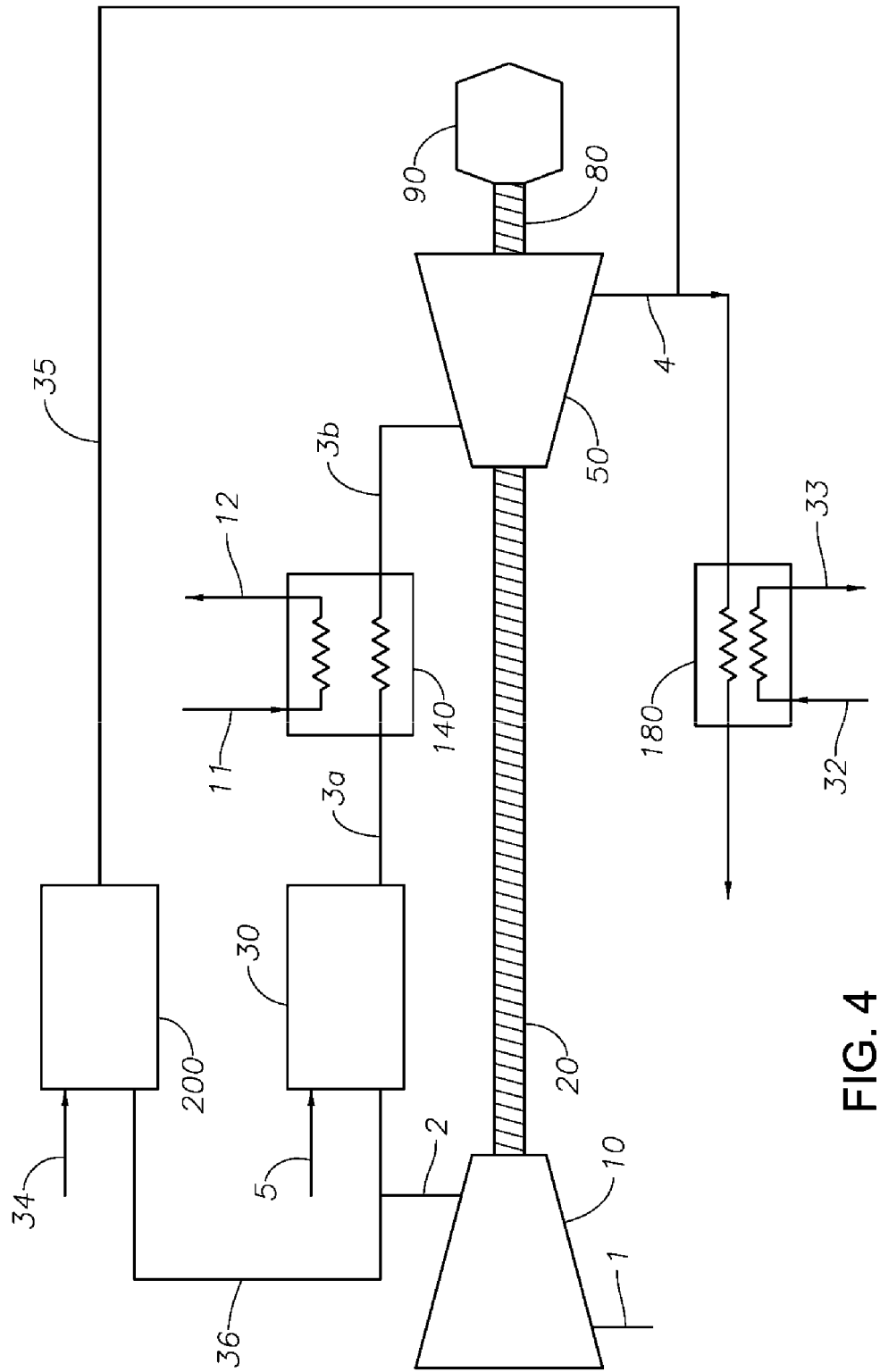
FIG. 4 is a schematic representation of an open-cycle gas turbine utilizing supplemental heating of the gas turbine's expanded effluent.

Certain aspects of these embodiments are illustrated schematically in FIG. 4, where the compression and expansion are carried out in one or more gas turbines. Referring now to FIG. 4, a first mixture (the working fluid) comprising, e.g., atmospheric air, is conducted via conduit 1 to compression zone 10. At least first and second portions of the compressed first mixture are separated therefrom (e.g., by the compressed first mixture into first and second portions), with the first portion being conducted to heating zone 30 for heating the first mixture. In certain embodiments, (i) the first portion comprises ≥50.0 wt. % of the compressed first mixture, e.g., ≥75.0 wt. %, such as in the range of 80.0 wt. % to 99.9 wt. %, the weight percents being based on the weight of the compressed first mixture, and (ii) the second portion comprises <50.0 wt. % of the compressed first mixture, e.g., ≤25.0 wt. %, such as in the range of 0.1 wt. % to 20.0 wt. %, the weight percents being based on the weight of the compressed first mixture.

The first portion is conducted to heating zone 30, where heat is transferred to the compressed first mixture (a first transfer of heat). Conventional gas-turbine heating means can be utilized in the heating zone, but the invention is not limited thereto. As in the case of Embodiments I, for example, when the first mixture includes atmospheric air, e.g., ≥90.0 wt. % of atmospheric air based on the weight of the first mixture, the heating zone can comprise one or more combustion zones for at least partially combusting a fuel with at least a portion of the compressed first mixture's air. A fourth mixture comprising fuel can be conducted to the combustion zone via conduit 5, for example. Effluent from heating zone 30 is conducted to expansion zone 50 via conduit 3 (comprising segments 3a and 3b). Optionally, a reaction zone 140 (as described in Embodiments I) is located downstream of heating zone 30 and upstream of expansion zone 50. Expanded effluent is conducted away via conduit 4 from expansion zone 50.

The second portion is conducted via conduit 36 to supplemental heating zone 200 for transferring heat to the second portion. When the first mixture comprises oxidant, the supplemental heating zone can include one or more combustion zones. Fuel can be transferred to the combustion via conduit 34. Fuel can be provided in the form of a mixture, e.g., in a fifth mixture that has substantially the same composition as the fourth mixture. A second effluent is conducted away via conduit 35 and is combined with the first effluent (conduit 4)

downstream of the expansion zone 50. The combined expanded effluent and second effluent are conducted to reaction zone 180 for indirectly transferring heat from the combined effluents to the second mixture. Reaction zone 180 can be substantially the same as the reaction zone 140 described in Embodiments I, and can be operated under substantially the same conditions, e.g., thermal pyrolysis conditions including exposing the second mixture to a temperature $\geq 800°$ C., e.g., $\geq 1000°$ C., such as $\geq 1200°$ C., or $\geq 1400°$ C., such as in the range of 1200° C. to 1500° C.

The second mixture is conducted via conduit 32 to reaction zone 180, and a third mixture is conducted away from reaction zone 180 via conduit 33, the third mixture comprising e.g., at least a portion of the products of the conversion of the second mixture, unreacted second mixture, etc. The second mixture can comprise, e.g., $\geq 90.0$ wt. % alkane based on the weight of the second mixture. The mass ratio of first portion: second portion and the amount of fuel provided to supplemental heating zone 200 are selected to provide a sufficient mass of second effluent at a sufficient temperature, so that when the second effluent is combined with the first effluent, the desired conversion reactions of the second mixture can occur in reactor 180.

Process features having the same index numbers in FIG. 4 as those of FIGS. 3a-3d perform similar (or the same) functions. Components such as the gas turbine, the compression zone, the heating zone, the expansion zone, shafts, etc. can be substantially the same as those described in connection with Embodiments I, including optional features thereof. For example, a portion of the shaft power obtained from expansion zone 50 can be utilized for additional compression, e.g., for compressing at least a portion of the third mixture. When the third mixture comprises olefin, compression of the third mixture can be utilized as part of an olefin upgrading and/or recovery train.

In certain embodiments, (i) the working fluid comprises atmospheric air, e.g., $\geq 90.0$ wt. % air, based on the weight of the working fluid, (ii) the fourth mixture comprises $\geq 10.0$ wt. % fuel based on the weight of the fourth mixture, e.g., $\geq 90.0$ wt. % hydrocarbon based on the weight of the fourth mixture, and (iii) the fifth mixture comprising $\geq 10.0$ wt. % fuel based on the weight of the fifth mixture, e.g., $\geq 90.0$ wt. % hydrocarbon based on the weight of the fifth mixture. Optionally, one or more of (i) the compressing of the first mixture, the dividing of the compressed first mixture, the expanding of the first effluent, and the indirect transfer of heat from the combined effluents to the second mixture of step are conducted in one or more gas turbines. The third mixture can comprise $\geq 1.0$ wt. % $C_{2+}$ unsaturates that are produced by the thermal pyrolysis, based on the weight of the third mixture.

When the process is carried out in one or more gas turbines, the process can have one or more of the following optional features: (i) at least a portion of the power generated by the process is shaft power, (ii) the gas turbine has at least one drive shaft for conveying at least a portion of the shaft power from the expansion zone to the compressing zone, (iii) the first portion of the first mixture comprises $\geq 10.0$ wt. % oxidant based on the weight of the first portion, and the second portion comprises $\geq 10.0$ wt. % oxidant based on the weight of the second portion, (iv) the transfer of heat to the first portion includes exposing the first portion to a temperature $\geq 1.0 \times 10^{3°}$ C. by reacting $\geq 50.0$ wt. % of the fourth mixture's fuel, based on the weight of the fourth mixture's fuel, with at least a portion of the first portion's oxidant, and (v) the transfer of heat to the second portion includes exposing the second portion to a temperature $\geq 1.0 \times 10^{3°}$ C. by reacting $\geq 50.0$ wt. % of the fifth mixture's fuel, based on the weight of the fifth mixture's fuel, with at least a portion of the second portion's oxidant.

The efficiency improvements described in connection with Embodiments I, such as those illustrated schematically in FIGS. 3b, 3c, and 3d, can be utilized in Embodiments II. For example, one or more regenerators 120 can be utilized for preheating at least a portion of the compressed first mixture, with the regenerator being utilized for heating one or more of (i) the compressed first mixture, the first portion, or the second portion. One or more heat recovery steam generations 110 can be utilized upstream or downstream of reaction zone 180 (with respect to the flow of the expanded effluent), e.g., before and/or after the expanding of the first portion. When located upstream of reaction zone 180, the heat recovery steam generator can transfer heat to water (e.g., liquid water, steam, wet steam, etc.) from one or more of (i) the expanded effluent, (ii) the second effluent, or (iii) the combined effluent. When the conversion of the second mixture is exothermic, as can be the case where the second mixture contains propane and hydrogen is transferred away from the propane to produce propylene, it can be desirable to locate at least one heat recovery steam generator downstream of reaction zone 180 (downstream with respect to the flow of the expanded effluent) in order to utilize at least a portion of the heat liberated during the propane conversion to produce steam. The steam can be expanded in one or more steam turbines 150, to produce additional shaft power delivered by shaft 81, as described in Embodiments I and illustrated in FIGS. 3c and 3d. For example, shaft power from the gas turbine delivered via shaft 80 can be combined with the additional shaft power of shaft 81 to power a load 90, as in FIG. 3c of Embodiments I, in order to produce electricity. Alternatively, shafts 81 and 80 can be independent, as shown in FIG. 3d of Embodiments I.

III. Embodiments Utilizing Exothermic Reactions of the Second Mixture

Figure 5:
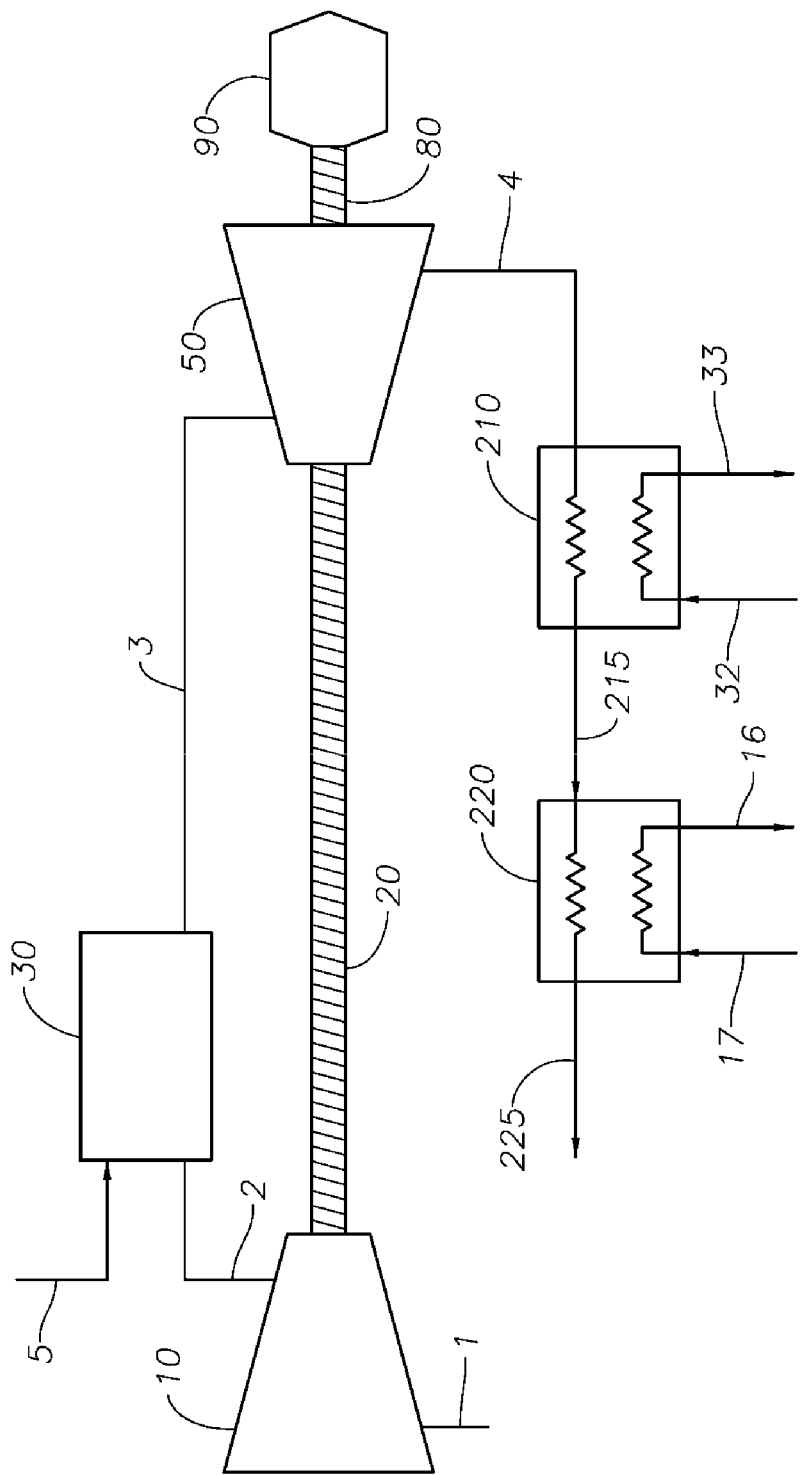
FIG. 5 is a schematic representation of an open-cycle gas turbine having two reaction stages downstream of the gas turbine's expansion zone.

In certain embodiments, the invention relates to a hydrocarbon conversion process utilizing an exothermic reaction to indirectly heat an expanded effluent. As in Embodiments I and II, Embodiments III utilize a first mixture (the working fluid) and a second mixture (a mixture comprising saturated hydrocarbon), the first mixture being in the vapor phase and the second mixture comprising $\geq 10.0$ wt. % of saturated hydrocarbon molecules based on the weight of the second mixture. As shown in FIG. 5, this includes compressing the first mixture (line 1) in compressing zone 10, transferring heat to the compressed first mixture (line 2) in heating zone 30 (with fuel being provided via line 5, for example) to produce an effluent (line 3), and expanding the effluent in expansion zone 50 to produce power, wherein at least a portion of the power is transferred to zone 10 by shaft 80 to be utilized for the compressing. Additional power can be transferred to load 90, e.g., one or more electric generators, via shaft 80. The process further comprises exothermically reacting the second mixture (line 32) in zone 210 to produce a third mixture (line 33), and indirectly transferring at least a portion of the heat from the exothermic reaction of zone 210 to the expanded effluent (line 4), with the heated expanded effluent conducted away via line 215.

Optionally the exothermic reaction of the second mixture includes producing a third mixture comprising $C_{2+}$ unsaturates, such as $C_{2+}$ olefins, by transferring hydrogen from at least a portion of the second mixture's saturated hydrocarbon, e.g., catalytic hydrogen transfer, oxidative dehydrogenation, oxidative coupling of methane, etc. The heated, expanded effluent is conducted away from zone 210 via one or more conduits 215. In certain embodiments, ≥90.0 wt. % of the saturated hydrocarbon comprises propane, based on the weight of the saturated hydrocarbon. The exothermic hydrogen transfer can be a catalytic hydrogen transfer, as described, e.g., in U.S. Pat. Nos. 5,639,926 and 5,585,530 which are incorporated by reference herein in their entirety.

In embodiments where the exothermic reaction of stage 210 includes one or more hydrogen transfer reactions, the second mixture conducted to stage 210 via line 32 can include at least one hydrogen-acceptor and at least one hydrogen-donor. The hydrogen-acceptor can comprise, e.g., at least one diene and/or acetylene alone or in admixture with at least one mono-olefin and/or at least one paraffin. Examples of suitable hydrogen-acceptors include propyne, propadiene, butadiene-1,2, butadiene-1,3, and mixtures thereof, for example, propyne plus propadiene; $C_4$ streams such as a mixed $C_4$ stream from a steam cracker; and $C_5$ gasoline, and/or pyrolysis gasoline, other streams from a cracker, etc. The hydrogen-donor can comprise, e.g., one or more straight-chain paraffins containing 4 or more carbon atoms ($C_{4+}$ straight-chain paraffins), for example, n-propane and/or n-butane. The hydrogen donor can optionally contain one or more branched chain paraffins such as i-butane.

The hydrogen transfer catalyst can include one or more noble metals, e.g., platinum and/or other platinum group metals such as palladium, on a support such as alumina; such catalysts modified with other species, such as Group IV elements including tin; chromia, alone or in conjunction with a platinum group metal or iron oxide. When used, the support can include, e.g., alumina, zirconia and/or alkaline earth oxides, especially those stabilized for use at high temperatures. The catalyst can be in sulfide form. The hydrogen transfer reaction is operated under exothermic operating conditions. The total pressure can be, e.g., in the range 0.3 bar absolute to 20 bar absolute, the partial pressure of hydrogen-donor plus hydrogen-acceptor can be, e.g., in the range of from 0.1 bar absolute to 20 bar absolute, and the temperature can be, e.g., in the range of from, e.g., 200° C. to 1000° C., such as 500° C. to 900° C. Hydrogen transfer catalyst and operating conditions can be the same as those disclosed for exothermic hydrogen transfer reactions in U.S. Pat. Nos. 5,639,926 and 5,585,530.

Optionally, zone 210 includes one or more tube reactors, with line 32 transferring the second mixture to the tube reactor and line 33 transferring the third mixture away from the tube reactor. The hydrogen transfer catalyst can be located, e.g., in one or more beds within the tube reactor, as a coating on the tube walls, etc., and combinations thereof.

The hydrogen transfer reaction is exothermic when the heat of hydrogenation of the hydrogen-acceptor is greater than the heat of dehydrogenation of the hydrogen-donor. The heat of dehydrogenation of a mole of hydrogen-donor can be approximated by subtracting the enthalpy (at the reaction temperature) of a mole of the hydrogen-donor from the sum of the enthalpies (at the reaction temperature) of a mole of hydrogen and a mole of the dehydrogenation product. The heat of hydrogenation of the hydrogen-acceptor can be approximated by multiplying the number of moles of hydrogen-acceptor hydrogenated by the heat of hydrogenation of a mole of hydrogen-acceptor, where the heat of hydrogenation of a mole of hydrogen-acceptor is obtained by subtracting the sum of the enthalpies (at the reaction temperature) of a mole of hydrogen and a mole of hydrogen-acceptor from the enthalpy (at the reaction temperature) of a mole of the hydrogenation product.

In embodiments where the exothermic reaction of stage 210 includes one or more oxidative dehydrogenation reactions, the reactions can include those described in Oxidative Dehydrogenation of Ethane and Propane at Short Contact Time, Bozena Silverova, et al., Applied Catalysis A: General 276 (2004) pp. 17-28, which is incorporated by reference herein in its entirety.

Suitable catalysts and operating conditions for the oxidative dehydrogenation reaction include those disclosed in the Silverova article, such as catalysts containing platinum group metals such as Pt and Rh. As in Embodiments I and II, the second mixture conducted to the exothermic reaction zone of stage 210 via line 32 can comprise, e.g., (i) one or more alkanes, such as ethane and/or propane, and (ii) one or more oxidants (such as molecular oxygen). Reactor temperature can be controlled, e.g., by regulating the second mixture's C/O mass ratio (on an atom basis). As in the embodiments utilizing exothermic hydrogen transfer, the amount of heat transferred to the expanded effluent of line 4 in stage 210 depends on the amount of heat released by the exothermic reaction. Suitable reaction condition and the amount of heat released by the reactions are disclosed in the Silberova article, with the oxidative dehydrogenation of ethane being slightly less exothermic ($\Delta H°_{298}$ of −105 kJ/mole) than the oxidative dehydrogenation of propane ($\Delta H°_{298}$ of −117 kJ/mole). Molecular oxygen can be obtained, e.g., from the expanded effluent of line 4. This can be desirable when the gas turbine's working fluid comprises air. The combustion of zone 30 and any supplemental combustion upstream of stage 210 converts a portion of the molecular oxygen in the air to oxidized carbon molecules, which leads to the expanded effluent in line 4 having less molecular oxygen than does ambient air. When the second mixture's oxidant comprises a portion of the expanded effluent, the lessened molecular oxygen content is believed to suppress conversion of the second mixture to oxidized carbon molecules, resulting in a greater yield of $C_{2+}$ unsaturated molecules in the third mixture.

Operating conditions for the exothermic oxidative dehydrogenation reactions include a temperature in the range of from about 200° C. to about 1100° C., e.g., about 400° C. to about 1000° C., with the highest propylene yield obtained at about 850° C. and the highest ethylene yield at about 950° C.

Figure 6:
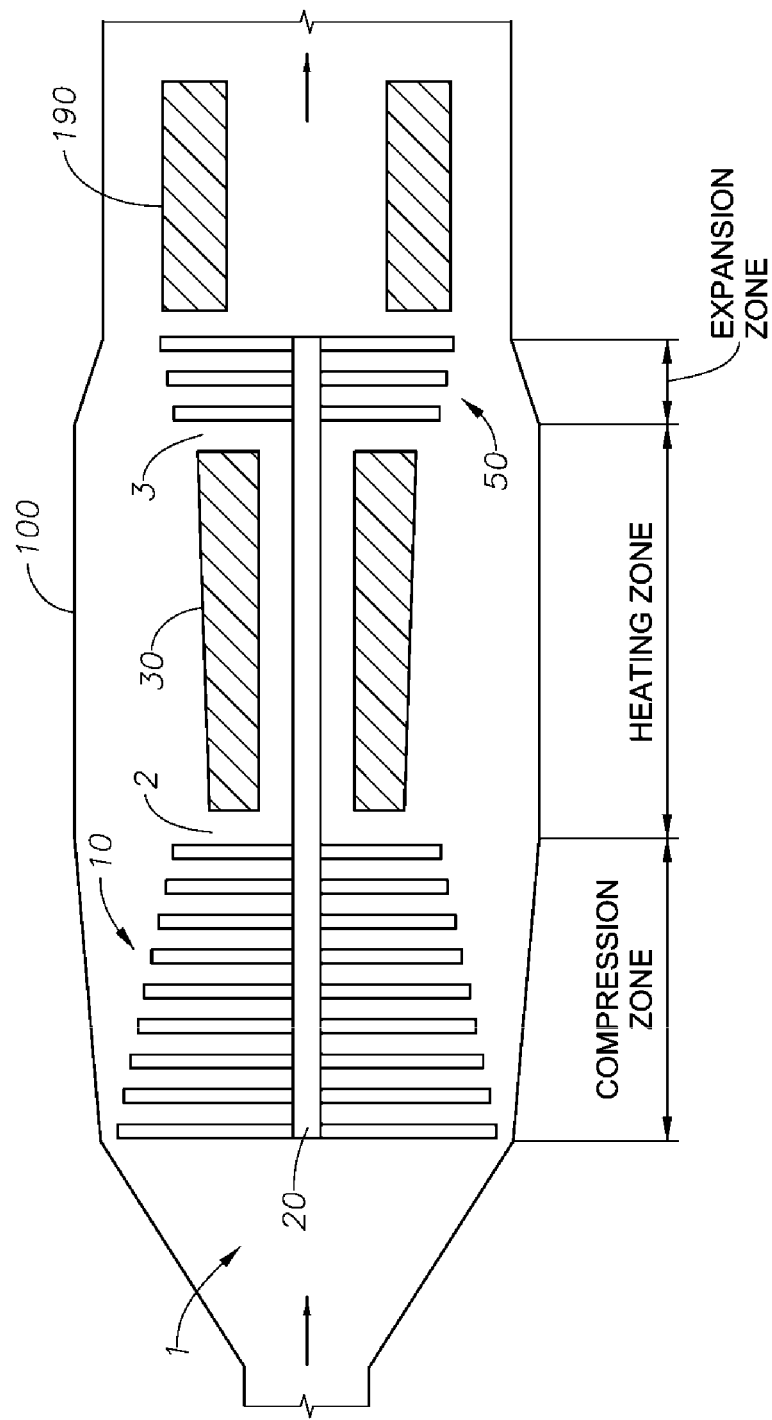
FIG. 6 is a schematic representation of a gas turbine unit having a supplemental duct firing zone downstream of the gas turbine's expansion zone.

Although stage 210 can include catalytic hydrogen and/or oxidative dehydrogenation reactions, the operation of stage 210 is not limited to these reactions, and the foregoing description is not meant to foreclose other exothermic reactions within the broader scope of the invention. For example, the exothermic reaction can also include oxidative coupling of one or more alkanes, such as methane. The oxidative coupling reactions can include those where methane is reacted with oxygen at a temperature in the range of about 500° C. to about 900° C. in the presence of a catalytically effective amount of at least one catalyst having activity for oxidative coupling. Effluent from the oxidative coupling reaction can comprise, e.g., ethylene and ethane. Optionally, substantially no heat is added to the expanded effluent of line 4 before the exothermic reaction of the second mixture in stage 210. In other embodiments, supplemental heating, such as supplemental duct firing zone 190 downstream of the gas turbine's expansion zone (schematically illustrated in FIG. 6), is utilized before the exothermic reaction of the second mixture. Features in FIGS. 2c and 6 performing the same or similar functions are identified by the same index numbers.

In certain embodiments, sufficient heat is added in stage 210 to produce a heated, expanded effluent having a temperature ≥750° C., e.g., ≥850° C., such as ≥950° C. For example, the heated expanded effluent of conduit 215 can have a temperature in the range of from about 700° C. to about 1200° C., e.g., about 800° C. to about 1000° C. In these embodiments, at least a portion of the heated, expanded effluent can be conducted to zone 220, where heat can be indirectly transferred from the heated, expanded effluent to a hydrocarbon-containing feed to produce higher-value products. Steam cracker feed, e.g., a mixture of one or more hydrocarbons and water, is an example of a hydrocarbon-containing feed provided to stage 220. The hydrocarbon-containing feed can be conducted to stage 220 via conduit 17, and at least a portion of the feed is converted, e.g., by steam cracking at a temperature in the range of 700° C. to about 1200° C. to produce $C_{2+}$ olefins, the olefins can be conducted away from stage 220 via line 16, together with, e.g., other products of the steam cracking, unconverted feed, etc. These embodiments can obviate the need for the supplemental firing utilized in U.S. Pat. No. 4,287,377. The expanded effluent is conducted away from stage 220 via conduit 225.

Although these are not shown in FIG. 5, the embodiments utilizing stage 210 and 220 are compatible with and can be utilized in combination with the features of any of the preceding embodiments, such as those illustrated in FIGS. 2b, 2c, 3a-3d, and/or 4. For example, the process can further comprise producing steam by indirectly transferring heat to water from one or more of (i) the third mixture, (ii) the effluent, or (iii) the expanded effluent. Optionally, at least a portion of the expanded effluent is conducted via line 225 to one or more heat recovery steam generators 110 for operating one or more steam turbines (in a similar way to that shown in FIGS. 3c and 3d). Since conventional olefin recovery from steam cracker effluent involves effluent compression, at least a portion of the steam turbine's power, e.g., ≥50.0% of the steam turbine's shaft power, can be advantageously utilized for powering the effluent's compressor train. Optionally, the process features one or more of (i) the power produced by the expansion includes shaft power, (ii) at least a portion of steam produced from the indirect transfer of heat is expanded in a steam turbine to produce additional shaft power; or (iii) ≥10.0% of the shaft power and/or ≥10.0% of the additional shaft power is converted to electricity.

Particular embodiments utilizing at least two hydrocarbon conversion reactions will now be described in more detail. The invention is not limited to these embodiments, and this description is not meant to foreclose other embodiments within the broader scope of the invention.

IV. Embodiments Utilizing Two or More Hydrocarbon Conversion Reactions

In certain embodiments, at least two hydrocarbon conversion reactions are performed, e.g., hydrocarbon pyrolysis and hydrocarbon hydrogen transfer. For example, a feed comprising one or more alkanes can be exposed to pyrolysis conditions, e.g., steam cracking conditions, in one or more pyrolysis tubes, with at least a portion of the heat for the pyrolysis being provided, e.g., by the indirect transfer of heat from effluent obtained from a gas turbine's heating zone 30. Unsaturated products of the pyrolysis, e.g., $C_{2+}$ unsaturates, can be utilized as hydrogen receptors in a second reaction, e.g., an alkane hydrogen transfer reaction, such as an exothermic, catalytic propane hydrogen transfer reaction, to produce propylene and ethylene. At least a portion of the heat obtained from the exothermic hydrogen transfer reaction can be indirectly transferred to an expanded effluent from one or more gas turbines. The heated effluent can be conducted to one or more heat recovery steam generators. At least a portion of the steam produced in the heat recovery steam generator can be utilized in one or more steam turbines for producing additional shaft power (in addition to the gas turbine's shaft power). At least a portion of the shaft power and/or at least a portion of the additional shaft power can be utilized for powering an electrical generator to produce electricity. In certain embodiments, the process can be operated more efficiently than those of Embodiments I or Embodiments III because the heat consumed by the endothermic pyrolysis reaction is at least partially restored to the process by the exothermic hydrogen transfer reaction.

EXAMPLES

Example 1

The following simulation is conducted, with reference to FIG. 3a. A working fluid comprising ≥99.0 wt. % of ambient air based on the weight of the working fluid is conducted to the compression zone 10 via conduit 1 at a rate of 500 kg/s. The ambient air has a temperature of 300° K ($T_1$) and a pressure of 1 bar absolute ($P_1$). The compressed air conducted away from zone 10 via conduit 2 has a temperature $T_2$ and a pressure of 5 bar absolute ($P_2$). Using the relationship $T_2=T_1*(P_2/P_1)^{(\gamma-1)/\gamma}$, with $\gamma=1.4$ (approximate value for air), $T_2$ is approximately 475° K.

10.9 kg/s of natural gas fuel is conducted to combustion chamber 30, where the fuel and a portion of the compressed air are combusted to produce heated compressed air having a temperature $T_3$ and a pressure $P_3$. The combustion produces a power $dQ/dt$ of $478 \times 10^6$ J/s. A value for $T_3$ of approximately 1426° K is obtained using the relationship $dQ/dt=C_p*(dm/dt)(T_3-T_2)$.

The heated compressed air is conducted to reaction zone 140 via conduit 3a. 10 kg/s (625 moles/s) of a feed comprising ≥99.0 methane based on the weight of the feed is conducted to zone 140 via conduit 11. Zone 140 contains a tube reactor, where the methane feed is located within the tube reactor's tubes and the heated compressed air is located outside the tube reactor's tubes. Heat is indirectly transferred through the walls of the tube from the heated compressed air to the methane feed, to convert the methane feed to acetylene, molecular hydrogen, and coke. Other products as would result in an actual reaction are ignored in this simulation. 0.67 wt. % of the methane feed is converted to the acetylene and molecular hydrogen by the reaction "A" $CH_4 \rightarrow \frac{1}{2} C_2H_2 + 1\frac{1}{2} H_2$, and 0.33 wt. % of the methane feed is converted to coke and molecular hydrogen by the reaction "B" $CH_4 \rightarrow C + 2H_2$, the weight percents being based on the weight of the methane feed. The enthalpy per mole of $CH_4$ for reaction "A" is approximately −188 kJ and for reaction "B" is approximately −74.6 kJ. Products of the methane conversion are conducted away from zone 140 via line 12. Compressed air having a temperature $T_4$ and a pressure $P_4$ are conducted away from zone 140 via line 3b to expansion zone 50. Per 625 moles of methane, approximately 78,000 kJ are required for reaction "A" and 16,000 kJ are required for reaction "B". Approximately $20 \times 10^6$ J/s of power is required to increase the temperature of 625 moles of methane feed in line 11 to the outlet temperature of zone 140 ($T_4$, which is approximately 1200° K), and the power consumed by reactions "A" and "B" is approximately $114 \times 10^6$ J/s.

The expanded air is conducted away from zone 50 via line 4, the expanded air having a temperature $T_5$ and a pressure $P_5$, where $P_5$ is approximately 1 bar absolute. In this simulation, there is no pressure drop for the compressed air across zone 140, i.e., $P_4$ is approximately 5 bar absolute. A $T_5$ value of approximately 758° K is obtained from the relationship $T_5=T_4*(P_5/P_4)^{(\gamma-1)/\gamma}$, where $\gamma$ has the value for air (1.4).

The shaft power provided to the turbo-expander by the expanding air is approximated by the relationship $(dW_t/dt)=C_p*(dm/dt)(T_4-T_5)=222 \times 10^6$ watts, where $C_p$ has the value for air. Since a power of 88×10⁶ watts is needed to compress the air in zone 10, an available shaft power (222×10⁶ watts–88×10⁶ watts) of 134×10⁶ watts is transmitted to load 90 via shaft 80, e.g., for producing electricity. Thermal efficiency is approximately 28%.

The simulation demonstrates that a gas turbine can be utilized for producing $C_{2+}$ unsaturates such as acetylene by methane pyrolysis in a tube reactor located between the gas turbine's combustion and expansion zones. Thermal efficiency is acceptable (28%), the process being only moderately less thermally efficient than a substantially similar gas turbine operated without the pyrolysis (37%). The additional power required for the pyrolysis is provided by combustion of an additional 2.1 kg/s of fuel in zone 30 to produce the 114×10⁶ J/s of power needed for the pyrolysis, which is well within the capabilities of conventional gas turbine combustors. If desired, thermodynamic efficiency can be improved e.g., by utilizing an exothermic reaction upstream of zone 140. For example, instead of combusting additional fuel, an exothermic oxidative dehydrogenation reaction is utilized upstream of zone 140 and downstream of zone 30 to provide 114×10⁶ J/s for pyrolysing 625 moles/s of methane in zone 140 under the specified conditions.

Example 2

The following simulation is conducted, with reference to FIG. 5. A working fluid comprising ≥99.0 wt. % of ambient air based on the weight of the working fluid is conducted to the compression zone 10 via conduit 1 at a rate of 500 kg/s. The ambient air has a temperature of 300° K ($T_1$) and a pressure of 1 bar absolute ($P_1$). The compressed air conducted away from zone 10 via conduit 2 has a temperature $T_2$ and a pressure of 5 bar absolute ($P_2$). A value for $T_2$ of approximately 475° K is obtained using the relationship $T_2=T_1*(P_2/P_1)^{(\gamma-1)/\gamma}$, with $\gamma=1.4$ (approximate value for air).

8.8 kg/s of natural gas fuel is conducted to combustion chamber 30, where the fuel and a portion of the compressed air are combusted to produce heated compressed air having a temperature $T_3$ and a pressure $P_3$. The combustion produces a power dQ/dt of 364×10⁶ J/s, and $T_3$ is approximately 1200° K. $P_3$ is approximately 5 bar absolute.

The heated compressed air is conducted to expansion zone 50 via conduit 3. The expanded air is conducted away from zone 50 via line 4, the expanded air having a temperature $T_4$ (approximately 758° K) and a pressure $P_4$ (approximately 1 bar absolute). The shaft power provided to the turbo-expander by the expanding air is approximately 222×10⁶ watts, where $C_p$ has the value for air. Since a power of 88×10⁶ watts is needed to compress the air in zone 10, an available shaft power (222×10⁶ watts–88×10⁶ watts) of 134×10⁶ watts is transmitted to load 90 via shaft 80, e.g., for producing electricity. Thermal efficiency is approximately 37%.

The expanded effluent is conducted via line 4 to stage 210, where the temperature of the expanded effluent is increased by transferring heat from an exothermic oxidative dehydrogenation reaction. Stage 210 is a tube reactor containing a monolithic Pt catalyst that is substantially the same as that disclosed in the Silberova article. Propane is conducted to stage 210 via conduit 32, and a product comprising propylene is conducted away via conduit 33. The propane flows through the tubes of the tube reactor, and heat is transferred through the tube walls to the expanded effluent.

A mixture comprising 69 kg/s of propane (approximately 1,568 moles/s) and 34.45 kg/s of molecular oxygen are conducted through the reactor tube of tube reactor 210. The total heat released is approximately 183×10⁶ J/s. Assuming perfect heat transfer, as in the simulation of Example 1, the temperature of the expanded air will increase to a temperature $T_5$ according to the relationship $dQ/dt=C_p$ (dm/dt) ($T_5-T_4$); resulting in a $T_5$ of approximately 1123° K (approximately 850° C.). The heated, expanded effluent is conducted via line 215 to stage 220, which comprises one or more zones (e.g., tube reactors) for steam cracking an ethane feed conveyed to stage 220 via conduit 17, with a reaction product comprising $C_{2+}$ unsaturates being conducted away via conduit 16. The steam cracking can be operated as disclosed in U.S. Pat. No. 4,287,377. Cooled expanded effluent is conducted away from stage 220 via conduit 225. The steam cracking conditions include exposing the ethane feed to a temperature of 850° C. under conventional ethane cracking conditions (ethane pyrolysis in the presence of steam).

This simulation demonstrates that a gas turbine can be utilized in combination with an exothermic reaction which (i) produces $C_{2+}$ unsaturates and (ii) heats the gas turbine's expanded effluent to a temperature which is sufficient for $C_{2+}$ alkane pyrolysis, such as steam cracking. Valuable $C_{2+}$ unsaturates are produced by the oxidative dehydrogenation reaction (stage 210) and by the steam cracking (stage 220), without a loss in gas turbine thermal efficiency.

All patents, test procedures, and other documents cited herein, including priority documents, are fully incorporated by reference to the extent such disclosure is not inconsistent and for all jurisdictions in which such incorporation is permitted.

While the illustrative forms disclosed herein have been described with particularity, it will be understood that various other modifications will be apparent to and can be readily made by those skilled in the art without departing from the spirit and scope of the disclosure. Accordingly, it is not intended that the scope of the claims appended hereto be limited to the example and descriptions set forth herein, but rather that the claims be construed as encompassing all the features of patentable novelty which reside herein, including all features which would be treated as equivalents thereof by those skilled in the art to which this disclosure pertains.

When numerical lower limits and numerical upper limits are listed herein, ranges from any lower limit to any upper limit are contemplated.

The invention claimed is:

1. A pyrolysis process of saturated hydrocarbons to produce olefins, comprising:
   (a) providing first and second mixtures, the first mixture being in the vapor phase and the second mixture comprising ≥10.0 wt. % of saturated hydrocarbon molecules based on the weight of the second mixture;
   (b) compressing the first mixture to produce a compressed first mixture;
   (c) dividing the compressed first mixture into at least first and second portions of the compressed mixture, wherein the first portion comprising ≥50 wt. of the compressed first mixture and the second portion comprising <50.0 wt. of the compressed first mixture;
   (d) dividing the second mixture comprising ≥10.0 wt. % of saturated hydrocarbon molecules into a first portion of the second mixture and a second portion of the second mixture;
   (e) transferring heat to the first portion of the compressed mixture in the first heating zone to produce a first heated portion of the compressed mixture;
   (f) pyrolyzing the first portion of the second mixture in the first pyrolysis reaction zone to convert the saturated hydrocarbons to olefins, wherein the pyrolysis of the first portion of the second mixture includes (i) an indirect transfer of heat between the first portion of the second mixture and the first heated portion of the compressed mixture and to yield a first heat-transferred portion of the compressed mixture and (ii) a conversion of ≥5.0 wt. % of the first portion of the second mixture's saturated hydrocarbon molecules, based on the weight of saturated hydrocarbon molecules in the first portion of the second mixture; to produce a first pyrolysis product containing olefins;

(g) expanding the first heat-transferred portion of the compressed mixture to produce power, wherein at least a portion of the power being utilized for the compressing;

(h) transferring heat to the second portion of the compressed mixture in the second heating zone to produce a second heated portion of the compressed mixture;

(i) combining ≥10.0 wt. % of the expanded first heat-transferred portion of the compressed mixture, with ≥10.0 wt. % of the second heated portion of the compressed mixture to produce a combined effluent; and (j) pyrolyzing the second portion of the second mixture in the second pyrolysis reaction zone to convert the saturated hydrocarbons to olefins, wherein the pyrolysis of the second portion of the second mixture includes (i) an indirect transfer of heat between the second portion of the second mixture and the combined effluent, and wherein the first pyrolysis and the second pyrolysis reaction are operated under substantially the same conditions to produce a second pyrolysis product containing olefins.

2. The process of claim 1, further comprising compressing at least a portion of the third mixture, the at least portion of the power being utilized for the compressing of the third mixture.

3. The process of claim 1, further comprising providing a fourth and fifth mixtures, the fourth mixture comprising ≥10.0 wt. % fuel based on the weight of the fourth mixture, and the fifth mixture comprising ≥10.0 wt. % fuel based on the weight of the fifth mixture, wherein:

(i) the compressing of step (b), the dividing of step (c), the pyrolysis of step (k), and the expanding of step (g) are conducted in a gas turbine;

(ii) the power is shaft power;

(iii) the gas turbine has at least one drive shaft for conveying at least a portion of the shaft power from step (g) to step (b);

(iv) the first portion of the dividing step (c) comprises ≥10.0 wt. % oxidant based on the weight of the first portion of the dividing step (c), and the second portion of the dividing step (c) comprises ≥10.0 wt. % oxidant based on the weight of the second portion of the dividing step (c);

(v) the heat transfer of step (e) includes exposing the first portion of the dividing step (c) to a temperature ≥$1.0 \times 10^{3}$° C. by reacting ≥50.0 wt. % of the fourth mixture's fuel, based on the weight of the fourth mixture's fuel, with at least a portion of the first portion's oxidant; and (vi) the heat transfer of step (h) includes exposing the second portion to a temperature ≥$1.0 \times 10^{3}$° C. by reacting ≥50.0 wt. % of the fifth mixture's fuel, based on the weight of the fifth mixture's fuel, with at least a portion of the second portion's oxidant.

4. The process of claim 3, wherein:

(i) the first mixture comprises ≥90.0 wt. % air, based on the weight of the first mixture;

(ii) the fourth mixture comprises ≥90.0 wt. % hydrocarbon based on the weight of the fourth mixture;

(iii) the second mixture comprises ≥90.0 wt. % alkane based on the weight of the second mixture.

5. The process of claim 1, further comprising converting at least a portion of the power to electricity.

* * * * *